United States Patent
Sun et al.

(10) Patent No.: US 11,253,175 B2
(45) Date of Patent: *Feb. 22, 2022

(54) APPARATUS, SYSTEMS, AND METHODS HAVING COMMON ELECTRONIC ARCHITECTURE FOR COMMUNICATING ANALYTE DATA

(71) Applicant: Ascensia Diabetes Care Holdings AG, Basel (CH)

(72) Inventors: Hoi-Cheong Steve Sun, Lexington, MA (US); Paul M. Ripley, Nanuet, NY (US); Mu Wu, Hopewell Junction, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 115 days.

This patent is subject to a terminal disclaimer.

(21) Appl. No.: 16/235,307

(22) Filed: Dec. 28, 2018

(65) Prior Publication Data
US 2019/0133503 A1    May 9, 2019

Related U.S. Application Data

(63) Continuation of application No. 12/944,259, filed on Nov. 11, 2010, now Pat. No. 10,201,296.

(51) Int. Cl.
*A61B 5/00* (2006.01)
*A61B 5/145* (2006.01)
(Continued)

(52) U.S. Cl.
CPC ........ *A61B 5/14532* (2013.01); *A61B 5/0024* (2013.01); *A61B 5/14735* (2013.01);
(Continued)

(58) Field of Classification Search
CPC combination set(s) only.
See application file for complete search history.

(56) References Cited

U.S. PATENT DOCUMENTS 5,575,403 A    11/1996    Charlton et al.
6,540,672 B1    4/2003    Simonsen
(Continued)

FOREIGN PATENT DOCUMENTS

CN    1348558 A    5/2002
CN    1921529 A    2/2007
(Continued)

OTHER PUBLICATIONS

Chinese Office Action of Chinese Application No. 201480076629.2 dated Sep. 9, 2019.
(Continued)

*Primary Examiner* — Shirley X Jian
(74) *Attorney, Agent, or Firm* — Dugan & Dugan, PC

(57) ABSTRACT

Embodiments provide apparatus, systems, and methods for communicating analyte data and/or related information. In a first aspect, the apparatus includes a transmitter/receiver unit which is configurable as either a transmitter or a receiver. The transmitter/receiver unit may be coupled to an on-body sensor and may be configured as a transmitter, or may be coupled to a management unit and may be configured as a receiver as part of a continuous analyte monitoring system. Analyte data communication systems and methods are provided, as are other aspects.

20 Claims, 15 Drawing Sheets

(51) Int. Cl.
  *A61B 5/1473* (2006.01)
  *A61B 5/15* (2006.01)
  *A61B 5/157* (2006.01)

(52) U.S. Cl.
  CPC ........... *A61B 5/157* (2013.01); *A61B 5/15087* (2013.01); *A61B 5/150969* (2013.01); *A61B 2560/0204* (2013.01); *A61B 2560/045* (2013.01); *A61B 2562/0295* (2013.01)

(56) References Cited

U.S. PATENT DOCUMENTS

| | | | |
|---|---|---|---|
| 6,558,320 B1* | 5/2003 | Causey, III | A61N 1/37235 |
| | | | 600/300 |
| 6,569,094 B2 | 5/2003 | Suzuki et al. | |
| 6,604,050 B2 | 8/2003 | Trippel et al. | |
| 6,607,484 B2 | 8/2003 | Suzuki et al. | |
| 6,674,821 B1 | 1/2004 | Mejyr | |
| 6,790,178 B1 | 9/2004 | Mault et al. | |
| 6,802,812 B1 | 10/2004 | Walker | |
| 6,819,013 B2 | 11/2004 | Kelly et al. | |
| 6,870,475 B2 | 3/2005 | Fitch et al. | |
| 7,039,420 B2 | 5/2006 | Koskinen et al. | |
| 7,286,894 B1 | 10/2007 | Grant et al. | |
| 7,316,648 B2 | 1/2008 | Kelly et al. | |
| 7,549,961 B1 | 6/2009 | Hwang | |
| 7,779,183 B2 | 8/2010 | Koehler et al. | |
| 8,131,564 B2 | 3/2012 | Dicks | |
| 8,208,973 B2 | 6/2012 | Mehta | |
| 8,483,974 B2 | 7/2013 | Connolly | |
| 8,579,813 B2 | 11/2013 | Causey et al. | |
| 8,682,598 B2 | 3/2014 | Connolly et al. | |
| 8,755,053 B2 | 6/2014 | Fright | |
| 8,758,245 B2 | 6/2014 | Ray et al. | |
| 8,895,316 B2 | 11/2014 | Batman et al. | |
| 8,954,007 B2 | 2/2015 | Hillyard | |
| 9,179,844 B2 | 11/2015 | Fright | |
| 9,439,566 B2* | 9/2016 | Arne | A61B 5/073 |
| 9,462,623 B2 | 10/2016 | Jakusovszky | |
| 9,696,980 B2 | 7/2017 | Dicks | |
| 9,750,896 B2 | 9/2017 | Kamen | |
| 9,861,285 B2 | 1/2018 | Fright | |
| 2005/0108057 A1 | 5/2005 | Cohen | |
| 2006/0009697 A1 | 1/2006 | Banet et al. | |
| 2006/0106433 A1 | 5/2006 | Mazar et al. | |
| 2006/0273930 A1 | 12/2006 | Godden | |
| 2007/0003061 A1 | 1/2007 | Jung et al. | |
| 2007/0027388 A1 | 2/2007 | Chou | |
| 2007/0181425 A1 | 8/2007 | Kim | |
| 2007/0293910 A1 | 12/2007 | Strother et al. | |
| 2007/0299480 A1 | 12/2007 | Hill | |
| 2008/0092638 A1 | 4/2008 | Brennenman et al. | |
| 2008/0109302 A1 | 5/2008 | Salokannel et al. | |
| 2008/0300919 A1 | 12/2008 | Charlton et al. | |
| 2009/0069642 A1 | 3/2009 | Gao et al. | |
| 2009/0116479 A1 | 5/2009 | Choi | |
| 2009/0138207 A1 | 5/2009 | Cosentino et al. | |
| 2009/0163793 A1 | 6/2009 | Koehler | |
| 2009/0213213 A1 | 8/2009 | Fright | |
| 2009/0240120 A1* | 9/2009 | Mensinger | G16H 40/67 |
| | | | 600/301 |
| 2009/0243791 A1 | 10/2009 | Partin | |
| 2010/0000862 A1 | 1/2010 | Rao | |
| 2010/0111066 A1 | 5/2010 | Mehta | |
| 2010/0113897 A1 | 5/2010 | Brennenman et al. | |
| 2010/0165795 A1 | 7/2010 | Elder | |
| 2010/0228111 A1 | 9/2010 | Friman | |
| 2011/0082711 A1 | 4/2011 | Poeze et al. | |
| 2011/0117841 A1 | 5/2011 | Thorn | |
| 2011/0124996 A1 | 5/2011 | Reinke et al. | |
| 2011/0165865 A1 | 7/2011 | Gao et al. | |
| 2011/0179405 A1 | 7/2011 | Dicks | |
| 2011/0256024 A1 | 10/2011 | Cole et al. | |
| 2011/0289497 A1 | 11/2011 | Kiaie | |
| 2011/0319813 A1 | 12/2011 | Kamen | |
| 2012/0019379 A1 | 1/2012 | Ben Ayed | |
| 2012/0123227 A1 | 5/2012 | Sun et al. | |
| 2012/0149245 A1 | 6/2012 | Ralston et al. | |
| 2012/0150556 A1 | 6/2012 | Galasso | |
| 2012/0238851 A1 | 9/2012 | Kamen | |
| 2012/0303638 A1 | 11/2012 | Bousamra | |
| 2013/0151266 A1 | 6/2013 | Randall | |
| 2013/0190674 A1 | 7/2013 | Case | |
| 2014/0012117 A1 | 1/2014 | Mensinger | |
| 2014/0039840 A1 | 2/2014 | Yuen et al. | |
| 2014/0149742 A1 | 5/2014 | Yau | |
| 2014/0266607 A1 | 9/2014 | Olodort | |
| 2014/0324445 A1 | 10/2014 | Carlsgaard | |
| 2014/0364056 A1 | 12/2014 | Belk | |
| 2014/0380218 A1 | 12/2014 | Refvik | |
| 2016/0337448 A1 | 11/2016 | Gofman et al. | |
| 2017/0030889 A1 | 2/2017 | Yao et al. | |
| 2017/0038847 A1 | 2/2017 | Schorsch | |
| 2017/0201931 A1 | 7/2017 | Swanzey et al. | |
| 2017/0208425 A1 | 7/2017 | Fu et al. | |
| 2017/0214780 A1 | 7/2017 | Gofman et al. | |
| 2017/0344718 A1 | 11/2017 | Chen | |
| 2018/0137937 A1 | 5/2018 | Gass et al. | |

FOREIGN PATENT DOCUMENTS

| | | |
|---|---|---|
| CN | 101675900 A | 3/2010 |
| CN | 201491011 U | 5/2010 |
| CN | 101816170 | 8/2010 |
| CN | 202075262 U | 12/2011 |
| CN | 101261276 B | 4/2012 |
| CN | 102422657 | 4/2012 |
| CN | 102565413 A | 7/2012 |
| CN | 202838653 U | 3/2013 |
| CN | 203311607 | 5/2013 |
| CN | 101431456 | 7/2014 |
| CN | 205006870 U | 2/2016 |
| CN | 103238154 B | 5/2016 |
| EP | 2741 528 A1 | 6/2014 |
| JP | H10-116460 | 5/1998 |
| JP | H10-170335 | 6/1998 |
| JP | 2003-173375 | 6/2003 |
| JP | 2003-216740 | 7/2003 |
| JP | 2004-154315 | 6/2004 |
| JP | 2007-111514 | 5/2007 |
| JP | 2008-186050 | 8/2008 |
| JP | 2011-019161 | 1/2011 |
| JP | 2012-230521 | 11/2012 |
| JP | 2013-201516 | 10/2013 |
| JP | 2014-038432 | 2/2014 |
| JP | 2014-164348 | 9/2014 |
| WO | WO0152727 | 7/2001 |
| WO | WO 2008/153825 | 12/2008 |
| WO | WO 2009/006486 | 1/2009 |
| WO | WO20110609232 A2 | 5/2011 |
| WO | WO 2012/128485 | 9/2012 |
| WO | WO2013009771 | 1/2013 |
| WO | WO2013066362 | 5/2013 |
| WO | WO 2014/146021 | 9/2014 |
| WO | WO2014-162549 | 9/2014 |
| WO | WO 2015/157582 | 10/2015 |
| WO | WO 2016/007186 | 1/2016 |
| WO | WO 2016/007187 | 1/2016 |
| WO | WO 2016/007188 | 1/2016 |
| WO | WO 2016/174206 | 11/2016 |

OTHER PUBLICATIONS

Taiwan Search report of related Taiwan Application No. 104123600 dated Jan. 24, 2019.
Chinese Office Action of Chinese Application No. 201480080414.8 dated Jul. 24, 2019.
Chinese Search report of Chinese Application No. 201480080414.8 dated Jul. 16, 2019.
International Search Report and Written Opinion of related International Application No. PCT/US14/69628 dated Mar. 11, 2015.
International Search report of related International Application No. PCT/US2014/062404 dated Mar. 5, 2015.

(56) References Cited

OTHER PUBLICATIONS

International Search Report and Written Opinion of related International Application No. PCT/US2014/062433 dated Mar. 23, 2015.
Mare, Shrirang, et al. "ZEBRA: Zero-Effort Bilateral Recurring Authentication", 2014 IEEE Symposium on Security and Privacy, IEEE, May 18, 2014, pp. 705-720.
Mayrhofer, R., et al., "Shake Well before Use: Intuitive and Securing Pairing of Mobile Devices", IEEE Transactions on Mobile Computing, IEEE Service Center, Los Alamitos, CA, US, vol. 8, No. 6, Jun. 1, 2009, pp. 792-806.
International Search Report and Written Opinion of related International Application No. PCT/US2014/062472 dated Mar. 23, 2015.
International Search Report and Written Opinion of related International Application No. PCT/US2015/025213 dated Jun. 15, 2015.
International Preliminary Report on Patentability of related International Application No. PCT/US14/69628 dated Jul. 21, 2016.
International Preliminary Report on Patentability of related International Application No. PCT/US2015/025213 dated Oct. 20, 2016.
International Preliminary report on Patentability of related International Application No. PCT/US2014/062404 dated Jan. 19, 2017.
International Preliminary Report on Patentability of related International Application No. PCT/US2014/062472 dated Jan. 19, 2017.
International Preliminary Report on Patentability of related International Application No. PCT/US2014/062433 dated Jan. 19, 2017.
International Search Report and Written Opinion of related International Application No. PCT/EP2016/059616 dated Jun. 2, 2016.
International Preliminary Report on Patentability of related International Application No. PCT/EP2016/059616 dated Nov. 9, 2017.
Chinese Search report of related Chinese Application No. 201580031100.3 dated Jul. 19, 2018.
Chinese Search report of related Chinese Application No. 201580031100.3 dated Apr. 10, 2019.
Chinese Search report of related Chinese Application No. 201480076629.2 dated Dec. 11, 2018.
Chinese Search report of related Chinese Application No. 201480076629.2 dated May 31, 2019.
Greenbaum, Dave: "Bluetooth Finder Helps You Find That Lost Device", Sep. 21, 2014 https://www.lifehacker.com.au/2014/09/bluetooth-finder-helps-you-find-that-lost-device (2014).

* cited by examiner

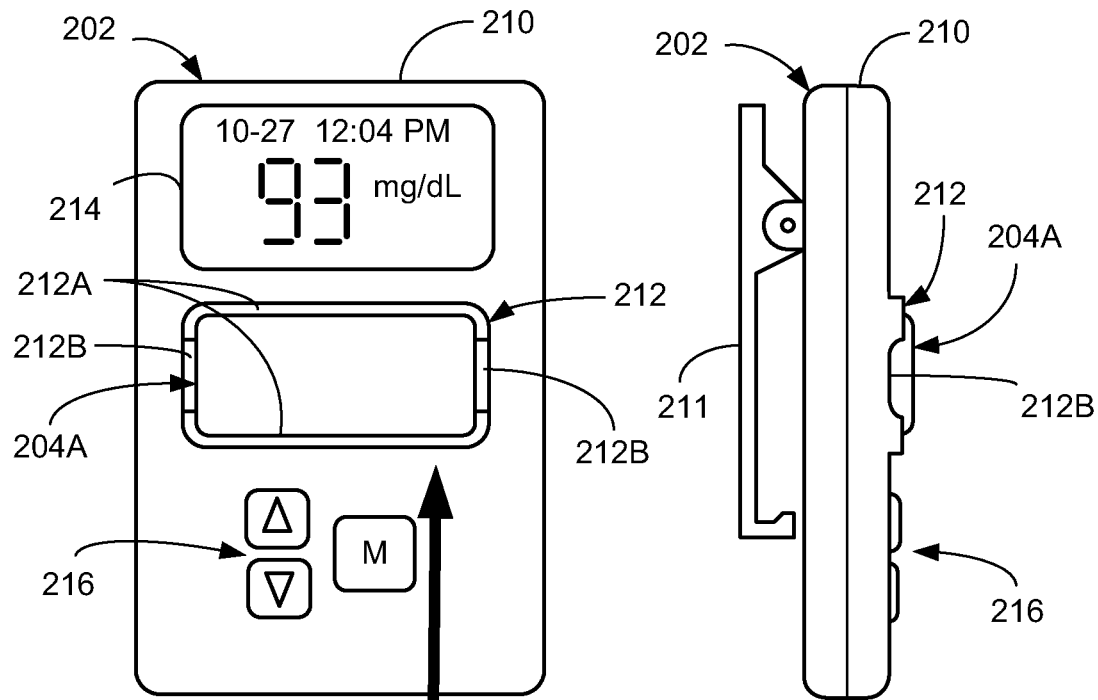
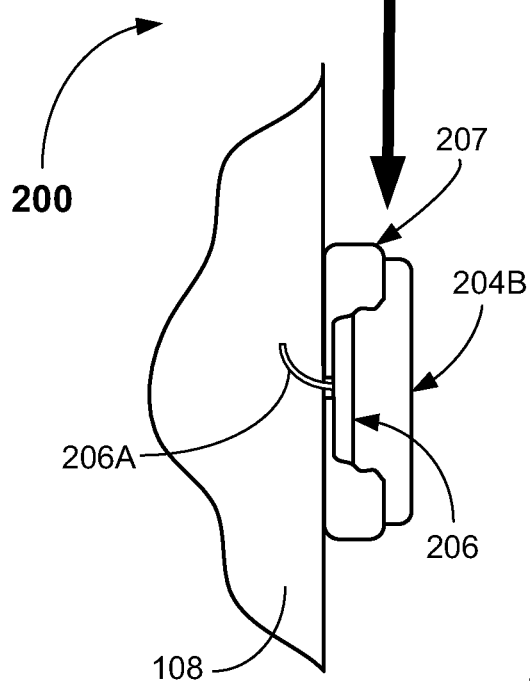
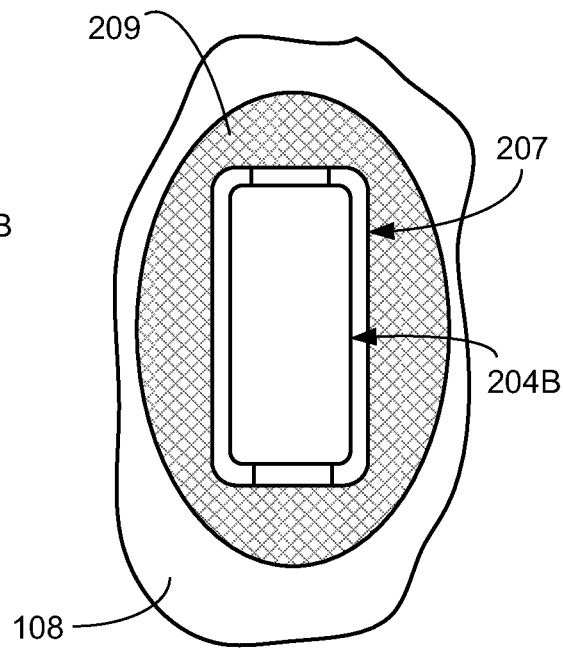
*FIG. 2A*
*FIG. 2B*
*FIG. 2C*

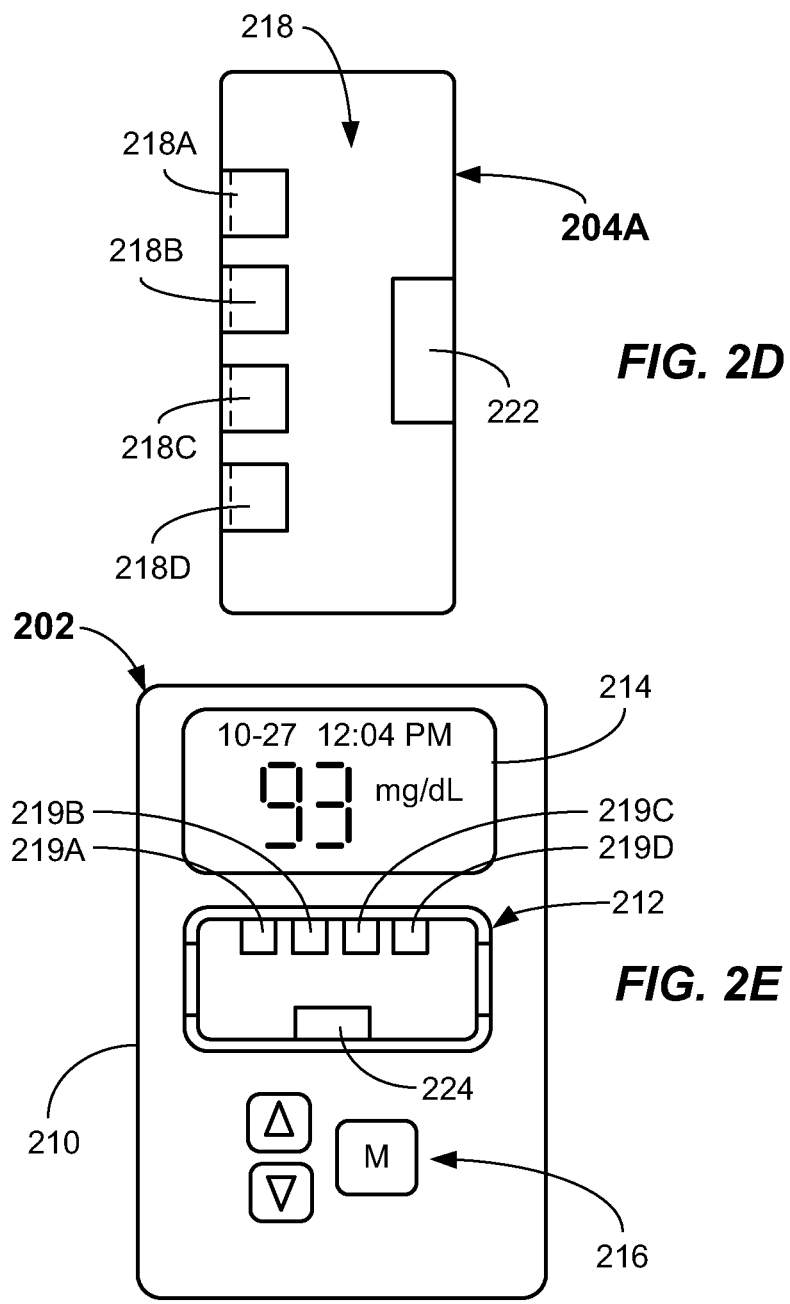

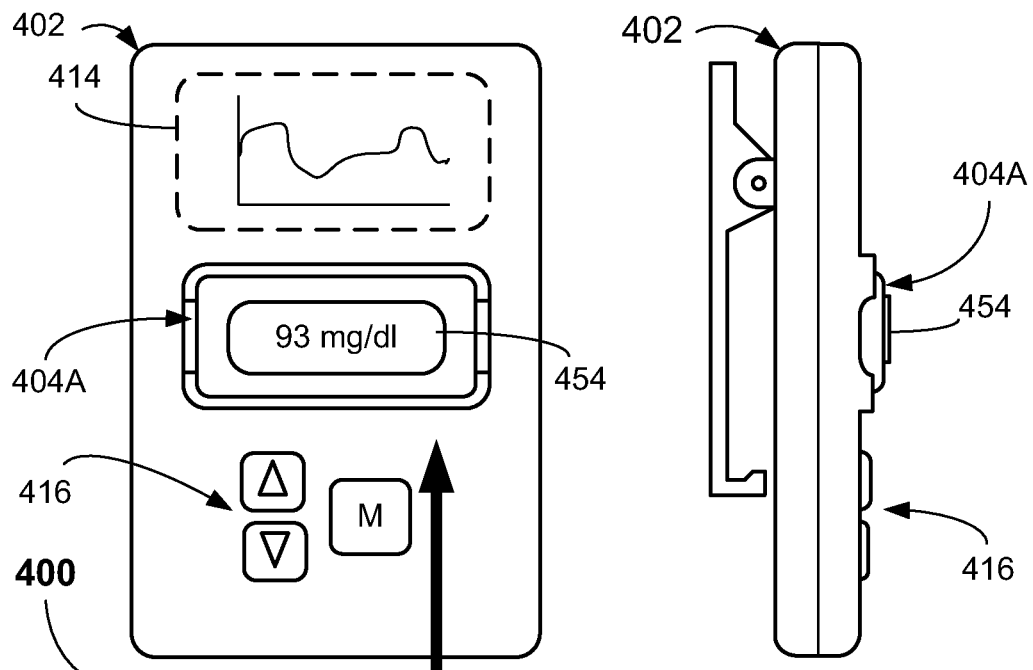
FIG. 4A
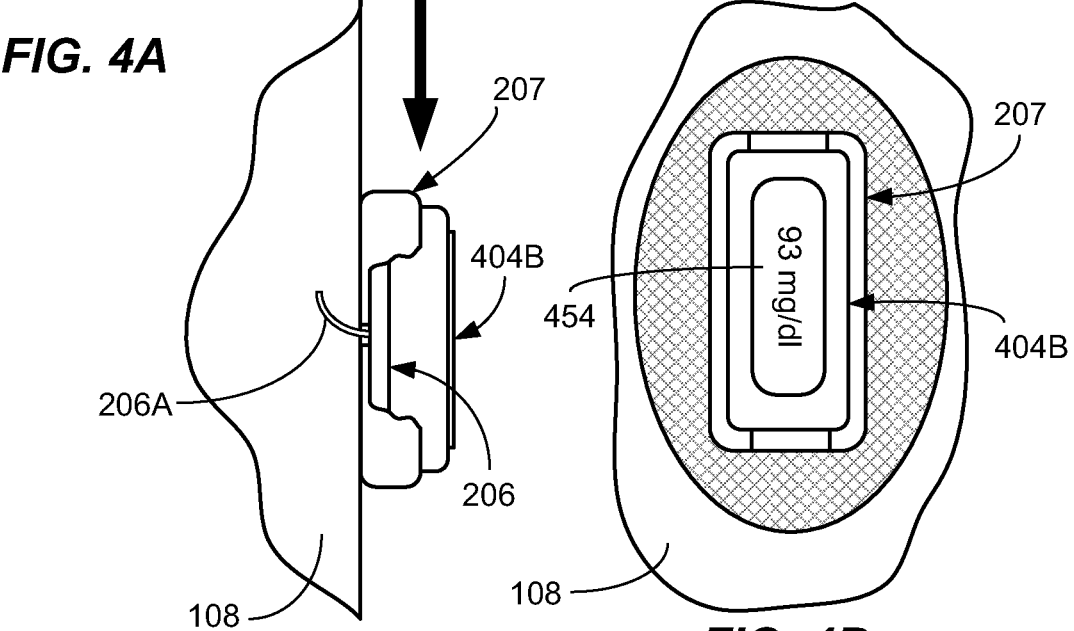
FIG. 4C
FIG. 4B

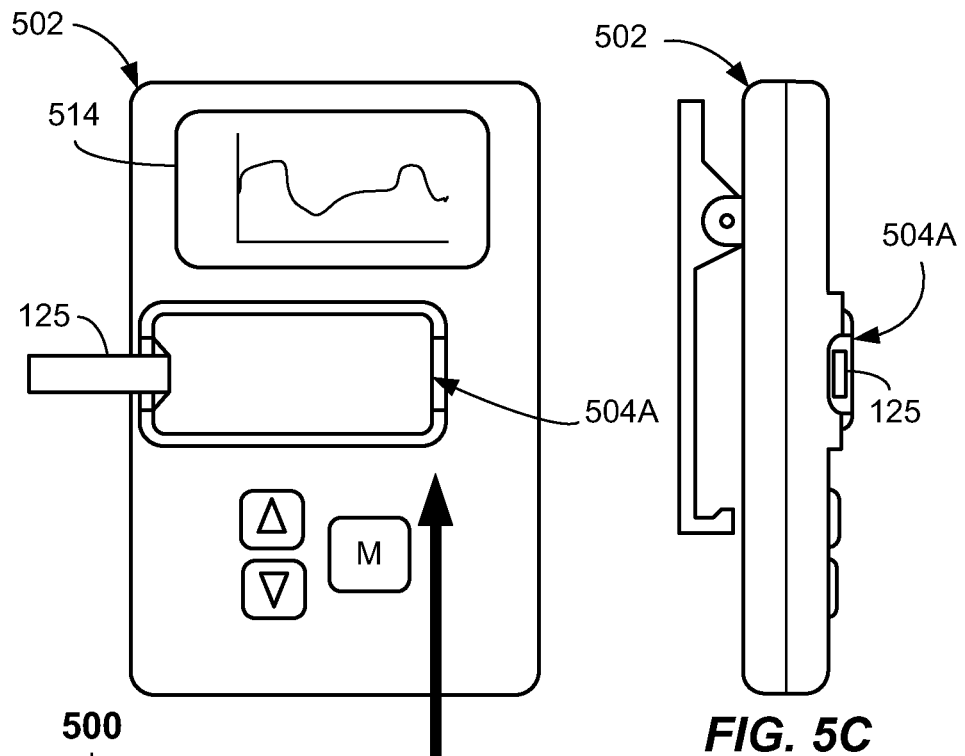
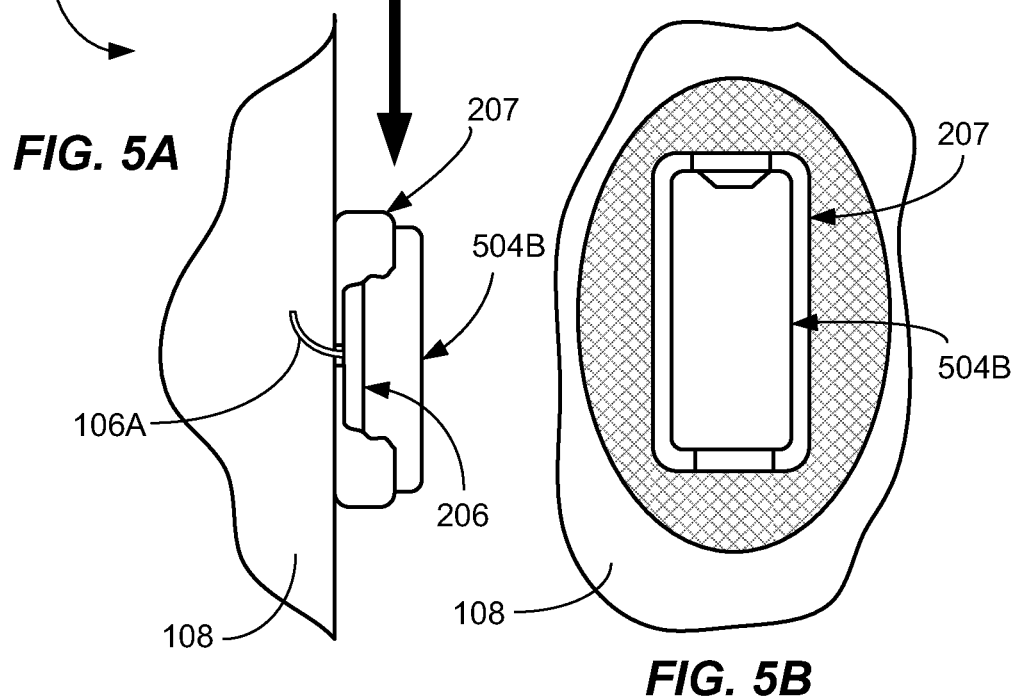
FIG. 5A
FIG. 5B
FIG. 5C

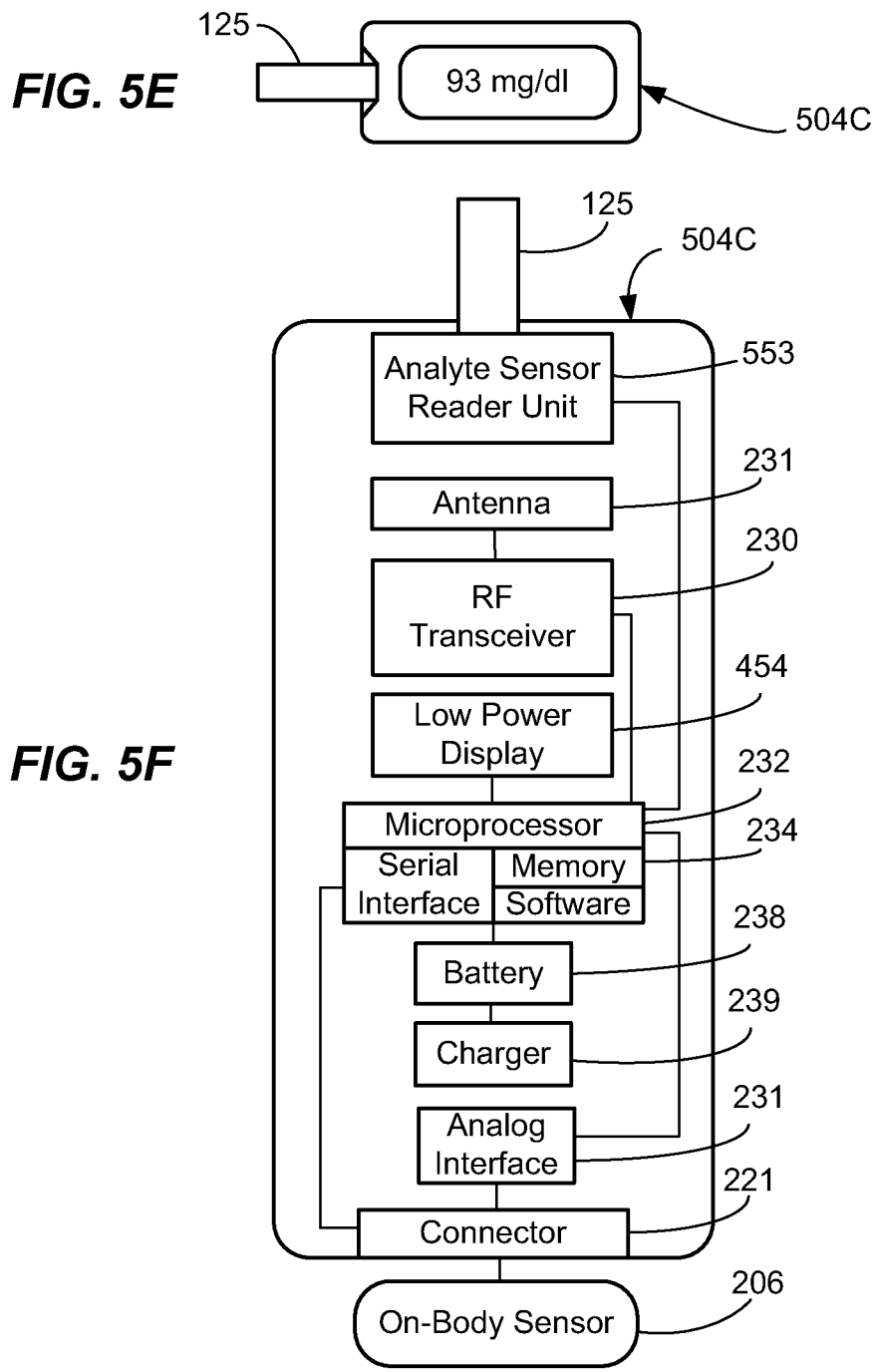

APPARATUS, SYSTEMS, AND METHODS HAVING COMMON ELECTRONIC ARCHITECTURE FOR COMMUNICATING ANALYTE DATA

RELATED APPLICATION

This is a continuation of U.S. patent application Ser. No. 12/944,259, filed Nov. 11, 2010, now U.S. Pat. No. 10,201,296, which is hereby incorporated by reference herein in its entirety for all purposes.

FIELD OF THE INVENTION

The present invention relates generally to apparatus, systems, and methods for communicating analyte data.

BACKGROUND OF THE INVENTION

The quantitative determination of analytes in bodily fluids may be important in the diagnoses and maintenance of certain physiological conditions. For example, individuals with diabetes frequently check their blood glucose levels. The results of such tests may be used to regulate their diets and/or to aid in determining whether to administer insulin or other medication.

Diagnostic systems, such as blood-analyte test systems, may employ a blood glucose meter (BGM) to calculate a blood glucose concentration level in a blood sample taken from a person. Such BGMs may operate by measuring an output, such as an electrical current or color change, resulting from a reaction with the analyte contained in the blood sample on a test sensor (e.g., a test strip). The measured test results typically may be stored by the BGM, and may be displayed to the user on the BGM in a simple numerical or graphical format. Basic operational systems of the BGM allow the user to access the test results directly thereon.

In other instances, users may more actively monitor their blood glucose levels through the use of a continuous glucose monitor (CGM). CGMs include a management unit, an on-body sensor, and a wireless transmitter coupled to the on-body sensor. The transmitter electrically couples with the sensor and transmits a wireless signal indicative of the blood glucose level to a receiver in the management unit, typically via RF technology.

To manage the CGM, a user may download a recent calibration reading, or manually input such a calibration reading, from a trusted BGM. In this manner, calibration of the CGM may be accomplished. Such systems include numerous components thereby making them quite complex, expensive, and bulky for the user to carry. Additionally, such components may be subject to becoming separated from one another, and a user may forget one or more of the components. Accordingly, apparatus, systems, and methods that may reduce system size and complexity may be desirable.

SUMMARY OF THE INVENTION

According to a first aspect, an analyte data communication system is provided. The analyte data communication system includes a first wireless transmitter/receiver unit adapted to be coupled to an on-body sensor and further adapted to transmit a wireless signal; and a second wireless transmitter/receiver unit adapted to be coupled to a management unit and adapted to receive the wireless signal transmitted from the first wireless transmitter/receiver unit wherein the first wireless transmitter/receiver unit and the second wireless transmitter/receiver unit may both be configured as either a transmitter or a receiver.

In a method aspect, a method adapted to communicate analyte data is provided. The communication method includes transmitting analyte data from a first interchangeable wireless transmitter/receiver unit coupled to an on-body sensor; and receiving the analyte data at a second interchangeable transmitter/receiver unit coupled to a management unit.

In an apparatus aspect, an analyte data communication apparatus is provided. The apparatus includes a wireless transmitter/receiver unit adapted to be connected to an on-body sensor or a management unit, and wherein the wireless transmitter/receiver unit is configurable as a transmitter, a receiver, or a stand-alone analyte meter.

In another apparatus aspect, an analyte data communication apparatus is provided. The apparatus includes a wireless transmitter/receiver unit adapted to be interchangeably coupled to an on-body sensor in a first configuration to transmit a wireless signal, and adapted to be interchangeably coupled to a management unit in a second configuration to receive a wireless signal.

In yet another apparatus aspect, an analyte data communication apparatus is provided. The apparatus includes a wireless transmitter/receiver unit adapted to be configured as a transmitter, a receiver, or a stand-alone analyte meter depending upon whether the wireless transmitter/receiver unit is coupled to an on-body sensor or coupled to a management unit.

Still other aspects, features, and advantages of the present invention may be readily apparent from the following detailed description which illustrates a number of exemplary embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention covers all modifications, equivalents, and alternatives falling within the scope of the invention.

BRIEF DESCRIPTION OF THE DRAWINGS

FIG. 2A is a block diagram illustrating an exemplary analyte data communication system including a reconfigurable transmitter/receiver unit according to embodiments of the invention.

FIG. 2B is a front view illustrating an exemplary transmitter/receiver unit configured as a transmitter according to embodiments of the invention.

FIG. 2C is a side view illustrating a management unit including the reconfigurable transmitter/receiver unit configured as a receiver according to embodiments of the invention.

FIG. 2D is a rear view illustrating a reconfigurable transmitter/receiver unit according to embodiments of the invention.

FIG. 2E is a front view illustrating a management unit having a holder adapted to receive the reconfigurable transmitter/receiver unit according to embodiments of the invention.

FIGS. 4A-4C are block diagrams illustrating another embodiment of an exemplary analyte data communication system according to the present invention.

FIGS. 5A-5C are block diagrams illustrating yet another embodiment of an exemplary analyte data communication system according to the present invention.

FIGS. 5E-5F are diagrams illustrating another embodiment of an exemplary reconfigurable transceiver/receiver unit having test sensor and display capability according to the present invention.

DETAILED DESCRIPTION

Figure 1:
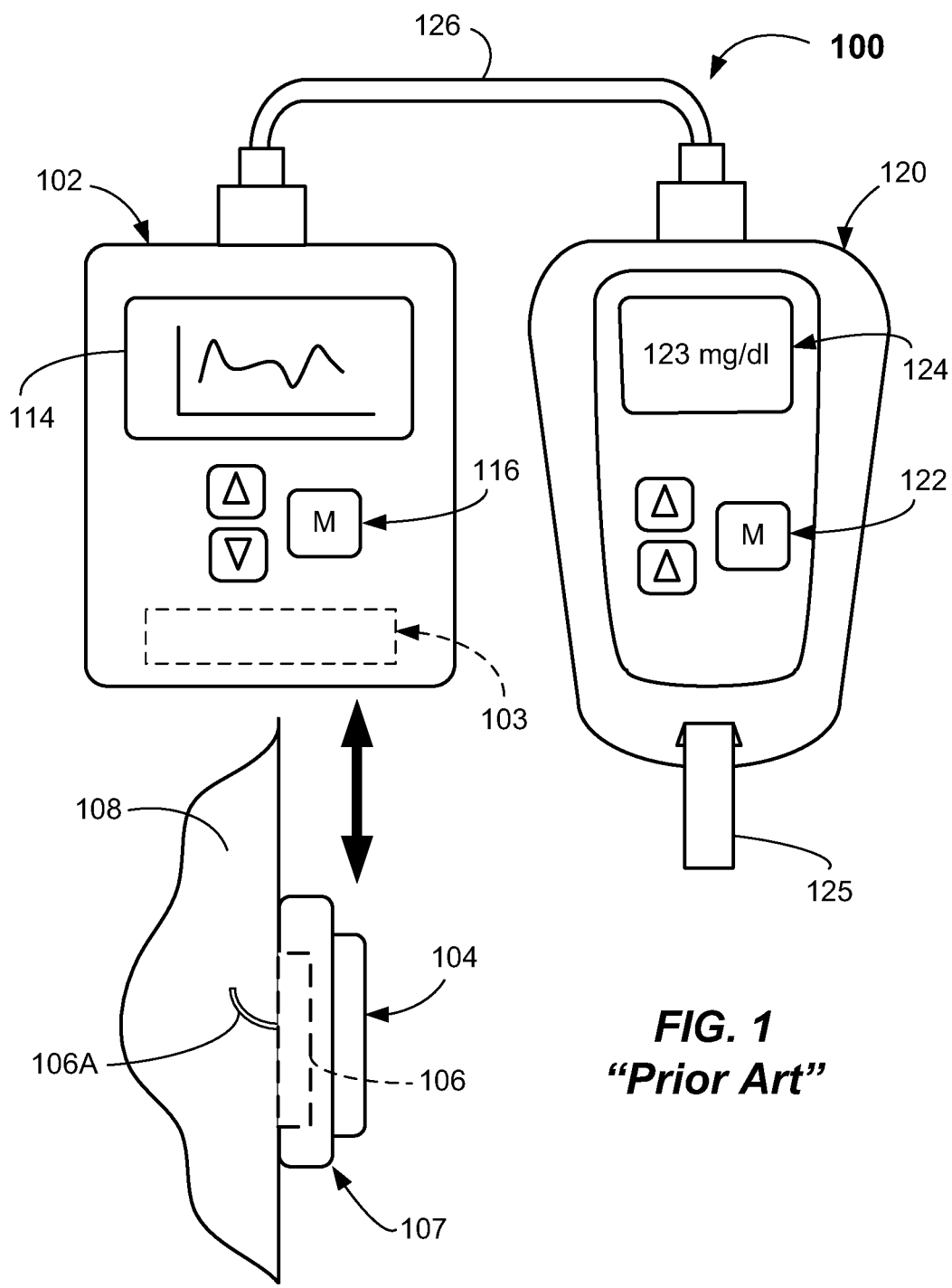
FIG. 1 is a block diagram illustrating an exemplary system including an analyte meter, continuous glucose monitor, and sensor/transmitter according to embodiments of the prior art.

A prior art continuous glucose monitoring (CGM) system 100 is described with reference to FIG. 1, wherein the CGM system 100 contains a management unit 102 including an internal receiver 103 (shown dotted), a transmitter 104 coupled to an on-body sensor 106 (also shown dotted), which is received in a sensor pod 107 mountable to a user's body 108 (e.g., torso). A canula, needle, or sensor component 106A is inserted into the user's body 108 through known means, such as use of an insertion set, and interfaces with the on-body sensor 106 to allow substantially continuous sensing of a blood glucose level in the user's blood. The management unit 102 has a display screen 114, which displays glucose readings and/or trends, and has a user interface 116 including a plurality of buttons for controlling various features of the management unit 102. The management unit 102 may be intermittently connected to a blood glucose meter (BGM) 120 to enable download of one or more calibration readings from the BGM 120 to the management unit 102. The BGM 120 also includes a user interface 122 and a display screen 124, and receives a test sensor 125 (e.g., a blood glucose test strip). The BGM 120 is connectable to the management unit 102 by a cable 126 to enable download of the calibration readings.

In view of the complexity of the prior CGM system 100, there is a need to reduce the component count and/or cost of such prior art CGM systems. To address this need, embodiments according to aspects of the present invention may provide an analyte data communication system including some interchangeable and/or common components.

In a first aspect, the analyte data communication system includes a first interchangeable wireless transmitter/receiver unit adapted to be coupled to an on-body sensor, and a second interchangeable wireless transmitter/receiver unit adapted to be coupled to a management unit. The first and second interchangeable transmitter/receiver units may be configurable to function as either a transmitter or a receiver. In some embodiments, the first and second transmitter/receiver units may be substantially identical. Accordingly, the first and second transmitter/receiver units may be detachable and may be interchangeable. The first and second interchangeable transmitter/receiver units may be reconfigured (e.g., by software) when interchanged. The first and second interchangeable transmitter/receiver units may be interchanged between the management unit and an on-body sensor pod.

According to some embodiments, when coupled to an on-body sensor of the analyte data communication system, the interchangeable wireless transmitter/receiver unit may be configured as a transmitter and may be adapted to transmit analyte data and/or related information obtained from the on-body sensor. When the interchangeable wireless transmitter/receiver unit is coupled to a management unit of the system, the interchangeable wireless transmitter/receiver unit may be configured as a receiver and may be adapted to receive analyte data and/or related information from the interchangeable transmitter/receiver unit configured as a transmitter.

Furthermore, when the interchangeable wireless transmitter/receiver unit is coupled to the management unit, the power source (e.g., battery) of the interchangeable wireless transmitter/receiver unit may be electrically charged by the power source (e.g., battery) of the management unit. Thus, the interchangeable wireless transmitter/receiver unit may be undergoing charging even when the management unit is not itself being charged. Therefore, according to one broad aspect, the interchangeable wireless transmitter/receiver unit may undergo charging, and may be made available as a fully-charged standby interchangeable transmitter/receiver unit, as the management unit is being worn by the user. Accordingly, the interchangeable wireless transmitter/receiver unit coupled to the management unit may be exchanged with the interchangeable wireless transmitter/receiver unit coupled to the on-body sensor on an as-needed basis.

In another broad aspect, the management unit or one or more of the interchangeable wireless transmitter/receiver units may include an integrated strip sensor reading unit whereby analyte calibration readings may be directly obtained by the management unit in addition to receiving analyte readings from the interchangeable and reconfigurable transmitter/receiver unit coupled to the on-body sensor. This may eliminate the need to carry a separate BGM for calibration purposes.

Advantageously, embodiments of the present invention may simplify the construction of the overall CGM system by utilizing a common interchangeable wireless transmitter/receiver unit. Furthermore, the present invention, in another aspect, may allow for a spare interchangeable wireless transmitter/receiver unit to be fully charged and ready for exchange with an interchangeable wireless transmitter/receiver unit coupled to the on-body sensor. Accordingly, in cases where the charge of the interchangeable wireless transmitter/receiver unit coupled to the on-body sensor becomes too low, it may be quickly and readily replaced.

These and other embodiments of apparatus, systems, and methods of the present invention are described below with reference to FIGS. 2A-9.

Referring now to FIGS. 2A-2F, a non-limiting embodiment of an analyte data communication system 200 adapted to communicate analyte data according to aspects of the invention is generally illustrated. The present analyte data communication system 200 may be used to transmit and receive blood glucose level readings, but is equally applicable to the measurement of any other type of analyte, such as concerning lipid profiles (e.g., cholesterol, triglycerides, LDL, and HDL), microalbumin, hemoglobin $A_{1C}$, fructose, lactate, keytones, bilirubin, or alcohol, or the like. The present invention may be applicable to transmission of other types of measured data (e.g., analyte data) as well.

In more detail, the analyte data communication system 200 includes a management unit 202, a first interchangeable wireless transmitter/receiver unit 204A adapted to be coupleable to the management unit 202, and a second interchangeable wireless transmitter/receiver unit 204B adapted to be coupleable to an on-body sensor 206. The second interchangeable wireless transmitter/receiver unit 204B may be detachably received from a sensor pod 207 (e.g., received in a recess thereof), which may also receive the on-body sensor 206. In the present embodiment, the second interchangeable wireless transmitter/receiver unit 204B may be retained in the sensor pod 207 by any suitable means. For example, the second interchangeable wireless transmitter/receiver unit 204B may be retained in the sensor pod 207 by clips or by any suitable connector 221. The connector 221 in some embodiments may provide an electrical connection to the on-body sensor 206 and also a mechanical retention. However, the present invention is not limited to the way in which the second interchangeable wireless transmitter/receiver unit 204B is attached to the sensor pod 207. Any form of detachable mechanism may be used, such as a locking, latching, or connecting mechanism or other connecting method. The electrical connection between the unit 204B and the sensor pod 207 may be sealed by a suitable sealing member, e.g., an o-ring or other type of seal. The sensor pod 207 and coupled on-body sensor 206 may be attached to the user's body 108 (e.g., the user's torso) by a suitable adhesive patch 209 (see FIG. 2B), which may be suitably secured to the sensor pod 207. Such adhesive patches and their construction are well known, and will not be further described herein. Any suitable construction of the sensor pod 207 may be employed. An insertion set or other insertion device may be used to insert a canula, needle, or sensor component 206A into the user's body 108. In operation, the canula, needle, or sensor component 206A provides a connection to the body fluid (e.g., interstitial fluid) from the user's body 108 to the on-body sensor 206, as is well known in the art.

The management unit 202 according to the invention is any device adapted to receive and process analyte data and/or related information from the on-body sensor 206. The management unit may be adapted to receive a continuous or semi-continuous flow of analyte data transmitted from the transmitter/receiver unit 204B. For example, in some embodiments, the management unit 202 may function as a continuous glucose monitor (CGM) receiving a continuous or semi-continuous flow of analyte data transmitted from the transmitter/receiver unit 204B coupled to the on-body sensor 206.

Exemplary embodiments of the management unit 202 may include a visual display 214 adapted to visually display analyte data and/or related information, which has been communicated/transferred from the interchangeable transmitter/receiver unit 204B (configured as a transmitter) to the interchangeable transmitter/receiver unit 204A (configured as a receiver). The visual display 214 may take on any form, such as any suitable digital or electronic display. Examples of suitable visual displays 214 include a Liquid Crystal Display (LCD), Light Emitting Diode (LED), Organic Light Emitting Diode (OLED), plasma, Chip-On-Glass (COG), Cathode Ray Tube (CRT), or the like. Other types of displays may be used. The visual display 214 may be adapted to communicate singular analyte data values, including dates and times associated therewith, as well as averages over any suitable time period (day, week, etc.). Other analyte data may be visually communicated.

The management unit 202 may include, for example, a user interface 216 including one or more of the following user operated interface components: keys, buttons, track balls, thumb wheels, or other conventional user-operated interface components to enable the user to interface with, and operate the functions of the management unit 202.

In some embodiments, such as best shown in FIG. 2A, an image containing the analyte data and/or related information may be displayed on the display 214 in close proximity in time (e.g., within about a second or two) of when the analyte data is actually received by the interchangeable transmitter/receiver unit 204A. Analyte data from analyte measurements undertaken by the on-body sensor 206 may be transmitted at any suitable interval, such as every few seconds, every minute, or every few minutes, for example. Other time intervals may be used. The displayed image of the analyte data and/or related information may be displayed on the display 214 for a few seconds, and then the screen may be caused to go blank until the next reading is received in order to save power.

The management unit 202 may include a housing 210, which may be formed from two pieces of suitable plastic (e.g., thermoplastic), for example. The housing 210 may contain or house all the working components shown in FIG. 2F, for example. Attached to a portion of the housing 210 may be a spring-loaded clip 211 to allow the management unit 202 to be worn by a user, such as by attachment to the user's belt or elsewhere on the user. Other types of attachment mechanisms, such as holsters and the like may be used so that the user may carry the management unit 202 along with them on their person.

Similar to the sensor pod 207, the housing 210 may include a recessed holder 212 into which the interchangeable transmitter/receiver unit 204A may be received. The holder 212 may include walls 212A that may closely receive the transmitter/receiver unit 204A, and may include clearance regions 212B at ends of the holder 212, which may allow the user's finger and thumb to access the interchangeable transmitter/receiver unit 204A for ease of detachment of and interchangeability of the interchangeable transmitter/receiver unit 204A from the holder 212. The attachment mechanism may be the same as described above for the attachment to the sensor pod 207. However, it should be understood that any suitable means for holding and/or locking the interchangeable transmitter/receiver unit 204A on the management unit 202 and holding and/or locking the interchangeable transmitter/receiver unit 204B on the on-body sensor pod 207 may be employed.

As best shown in FIG. 2D, an enlarged bottom view of the interchangeable transmitter/receiver unit 204A is illustrated. A surface 218 (e.g., a bottom surface) of the interchangeable transmitter/receiver unit 204A may include electrical contacts 218A-218D, which may form a connector 220 that interfaces with a connector 221 including electrical contacts 219A-219D (FIG. 2E) provided on the management unit 202. The electrical contacts 218A-218D or 219A-219D or both may include resilient and/or compressible contacts, for example. The contacts may be leaf springs or other resilient or spring-like components. However, any suitable electrical connection enabling connection to the management unit 202 may be used. The contacts 218A-218D, 219A-219D may allow for electrical connection between the components of the interchangeable transmitter/receiver unit 204A and the electrical components of the management unit 202. The interchangeable transmitter/receiver unit 204A may include a physical feature, such as a recess 222, which will only allow the insertion of the transmitter/receiver unit 204A into the holder 212 in one orientation. As shown in FIG. 2E, the management unit 202 may include an engaging protrusion 224, which may mate with the recess 222 when the interchangeable transmitter/receiver unit 204A is received in the holder 212 in a correct orientation. Other mechanisms for ensuring the proper insertion orientation of the transmitter/receiver unit 204A in the holder 212 may be used. In some embodiments, one or more of the connectors 220, 221 may include prongs which not only provide an electrical connection, but also provide mechanical retention.

Figure 2F:
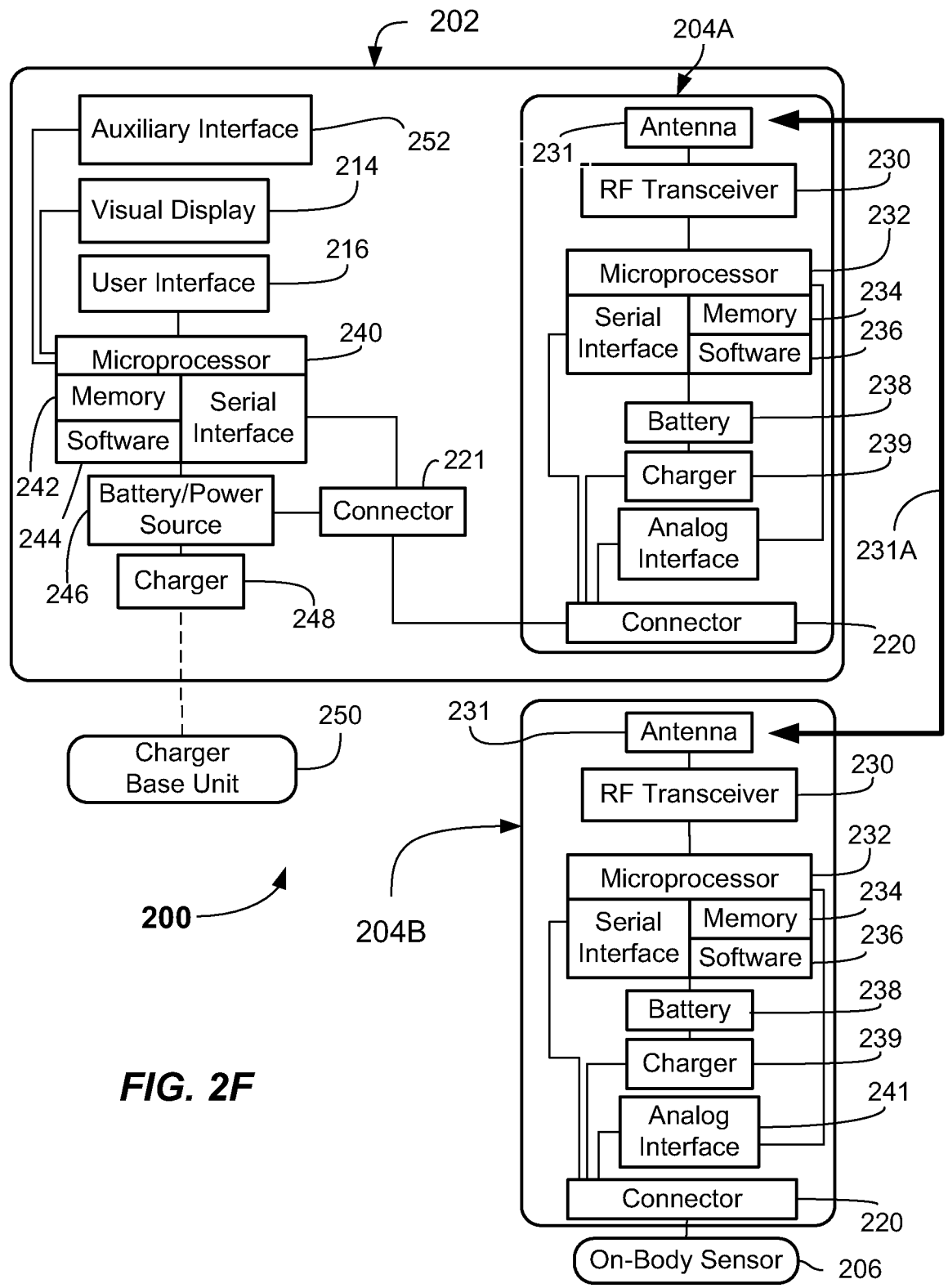
FIG. 2F is a block diagram illustrating an exemplary analyte data communication system according to embodiments of the present invention.
Figures 3A, 3B, 3C:
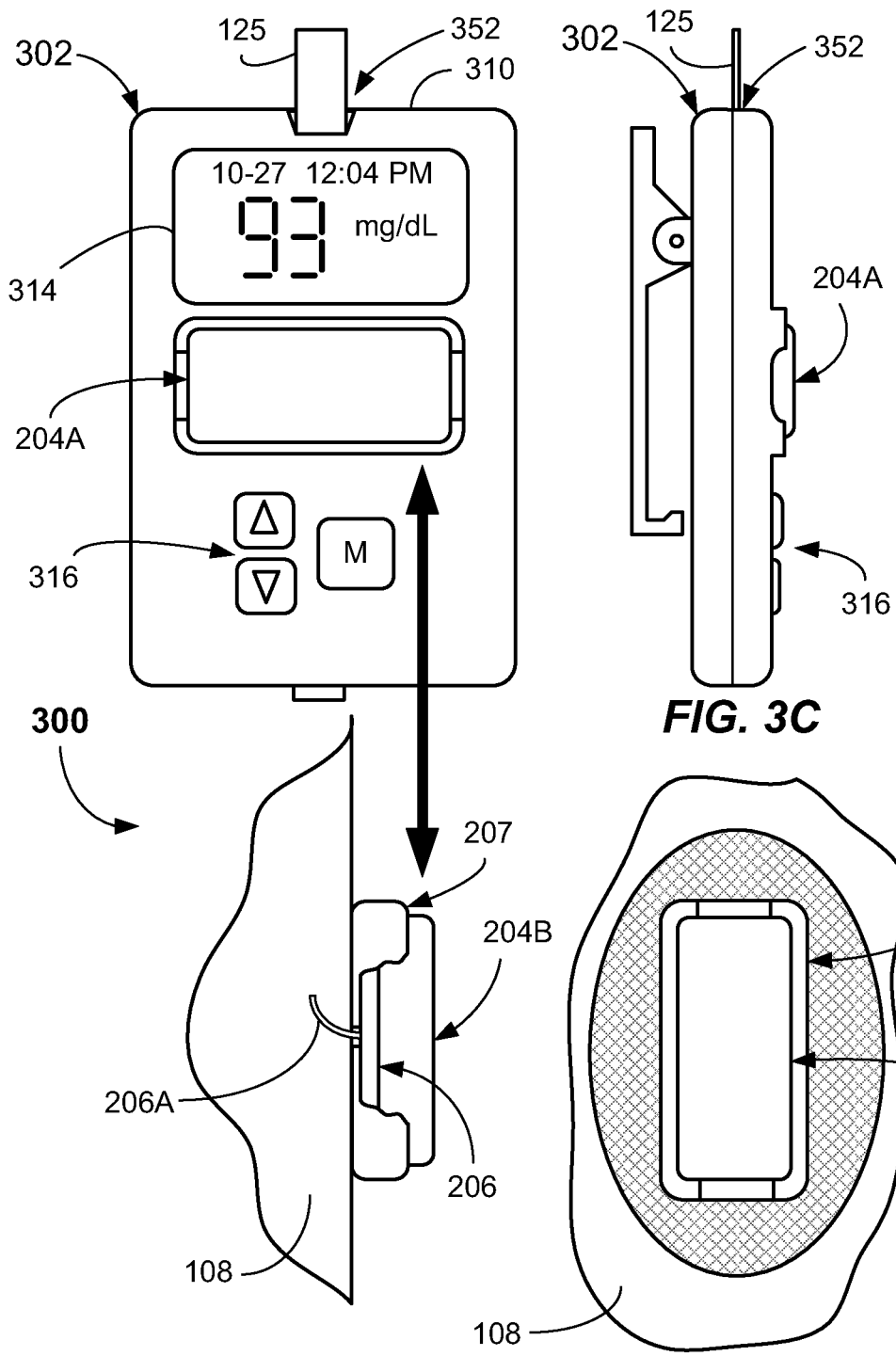
FIGS. 3A-3D are block diagrams illustrating another exemplary analyte data communication system having test strip reading capability in the management unit according to embodiments of the present invention.
Figure 3D:
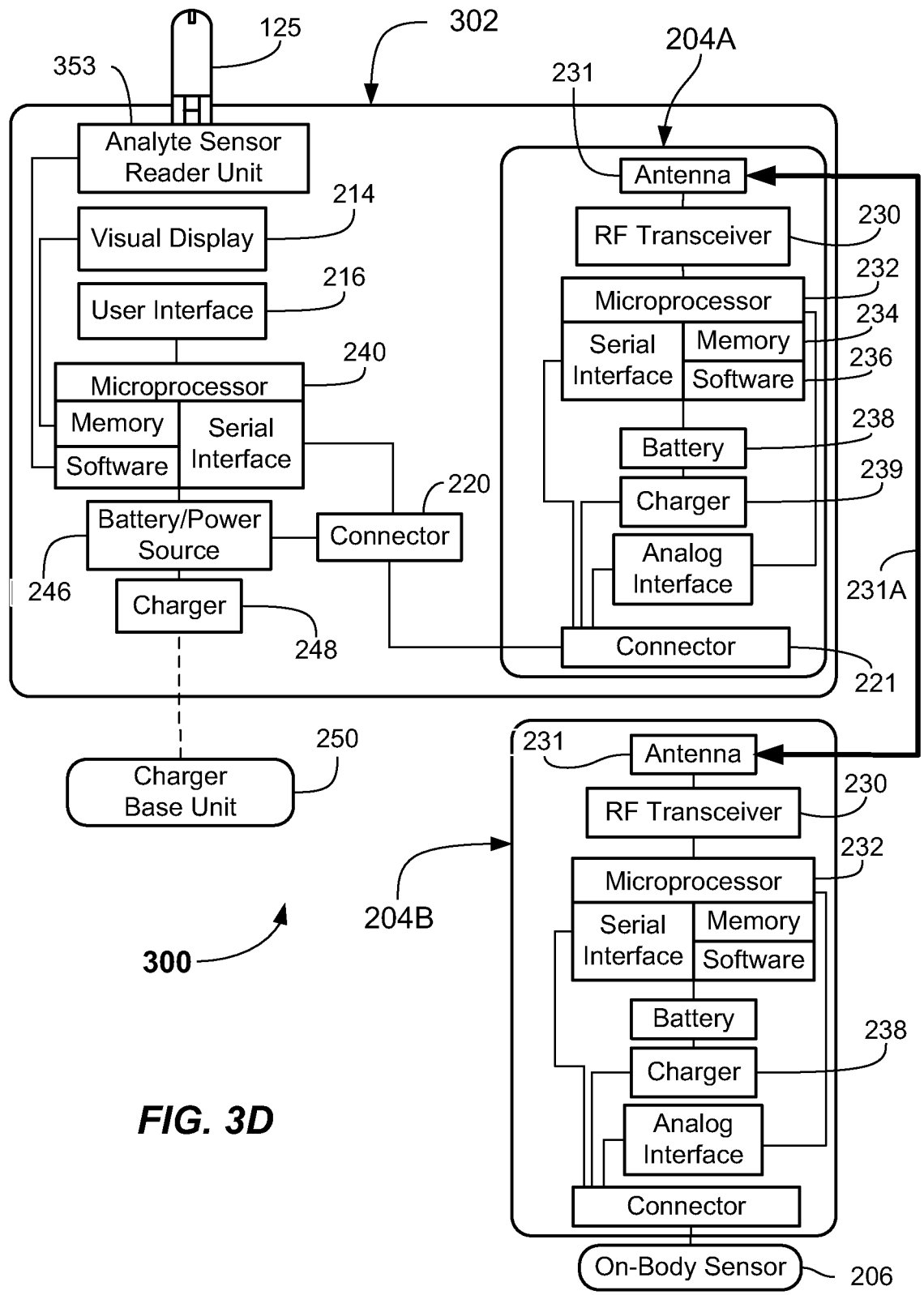
Figure 4D:
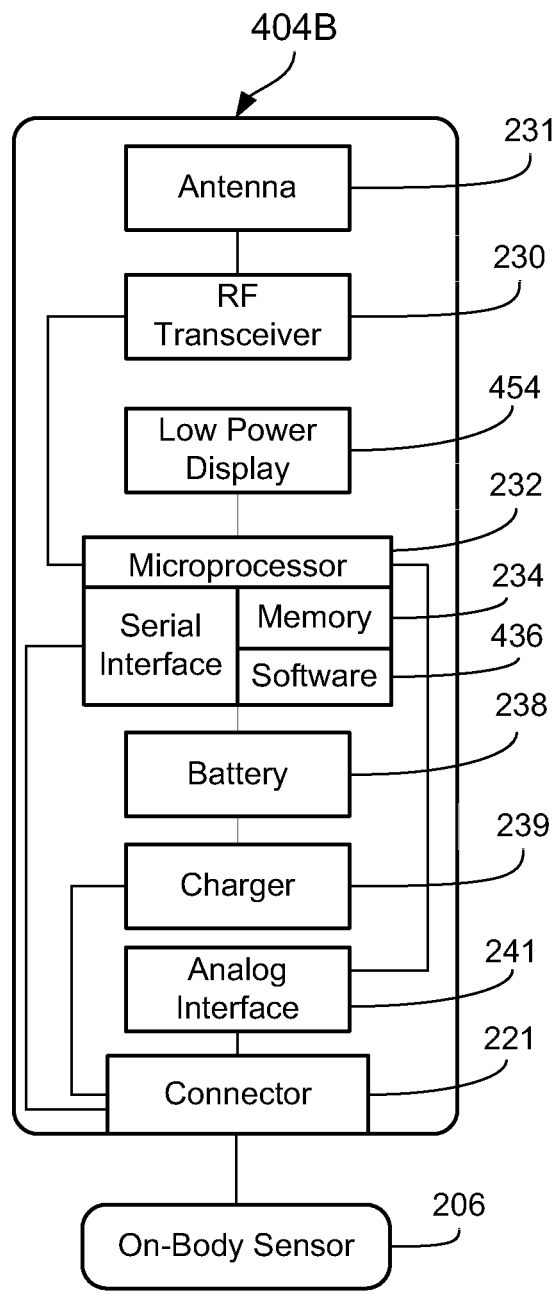
FIG. 4D is a block diagram illustrating another embodiment of an exemplary reconfigurable transceiver/receiver unit according to the present invention.

Now referring to FIG. 2F, the components of the first interchangeable transmitter/receiver unit 204A, the second interchangeable transmitter/receiver unit 204B, and the management unit 202 will be described in more detail. It should be recognized that the components of interchangeable transmitter/receiver unit 204A may be substantially identical to that of the interchangeable transmitter/receiver unit 204B. In a preferred implementation, the two are identical.

In more detail, the interchangeable transmitter/receiver units 204A, 204B may include a reconfigurable transceiver 230, which may carry out communication via BLUETOOTH, BLUETOOTH LE, ZIGBEE, ANT, or any other suitable communication standard or protocol. The interchangeable transmitter/receiver units 204A, 204B may be paired, i.e., by establishing knowledge of the identification of the other, such as by establishing a digital value identification (ID) that uniquely identifies each unit 204A, 204B and sending that ID with the data packet each time the units 204A, 204B communicate. Other wireless communications that do not include the ID are simply ignored. The pairing information may be transferred by docking each of the units 204A, 204B to the management unit 202 as part of the initial setup of the system 200, or the ID may be preset for the pair of units 204A, 204B at the factory. An antenna 231 electrically coupled to the reconfigurable transceiver 230 may be employed to transmit the signals to the interchangeable transmitter/receiver units 204A, 204B. The reconfigurable transceiver 230 may be any chipset or electronic component with an integrated transmitter and receiver, for example. The chipset may be a CC1110 available from Texas Instruments of Dallas, Tex., for example. Other types of chipsets may be used such as RF transceivers, which are low cost, multi-channel radios for low-power wireless applications, which may operate in the 2.4 GHz and sub-1 GHz frequency bands, for example.

The reconfiguration from a transmitter to a receiver may be carried out in software as further described herein with reference to FIGS. 6-9 herein. The reconfigurable transceiver 230 may interface with a digital processor 232 onboard the transmitter/receiver units 204A, 204B through any conventional means, such as by using a serial interface such as a 1-wire protocol from Dallas Semiconductor, or 2-wire protocols such as UART, and I2C, or multi-wire protocols such as SPI. The transceiver 230, interface, and digital processor 232 (e.g., microcontroller or microprocessor) may be provided on a printed circuit board, for example. The digital processor 232 may be any suitable component, such as an 8051 processor available from INTEL. However, in some implementations, the digital processor 232 may include additional user interface and data analysis capability.

In other embodiments, the digital processor 232 may be an ARM Cortex microprocessor available from ARM Inc. of San Jose, Calif. The digital processor 232 may function to: 1) calculate analyte values according to stored calculation algorithms, 2) interface with the memory 234, 3) receive inputs from the on-body sensor 206, 4) control the operation of the RF transmitter/receiver, 5) control the charging of the battery, and 6) control the processes of the interchangeable transmitter/receiver unit 204A, 204B, for example. In order to store the data received from the on-body sensor 206, the interchangeable transmitter/receiver units 204A, 204B may include a local memory 234. The memory 234 may be any suitable form of memory, such as a RAM, EEPROM, or flash memory, for example. Other types of memory may be used. The memory 234 may store software 236, which may include software components that may execute operations of the interchangeable transmitter/receiver unit 204A, 204B, such as telemetric protocols and communication, transmitter/receiver pairing, initialization, reconfiguration, charging, signal analyzer and data management and display. In order to provide suitable power to operate the various components of the interchangeable transmitter/receiver units 204A, 204B, a source of power may be provided, such as a battery 238. In the depicted embodiment, a rechargeable battery, such as a 3.7V lithium ion polymer rechargeable battery may be used. Other types of batteries may be used. The power source 238 may also include suitable power control electronics (e.g., a charger 239) to control the charging of the rechargeable battery. The analog interface 241 provides the necessary output voltage to the on-body sensor 206 and converts the low current output signal from the sensor 206 into a digital count for the processor 234.

The management unit 202 will now be described in more detail with reference to FIG. 2F. The management unit 202 may include an interchangeable transmitter/receiver unit 204A which may be an exact duplicate of the interchangeable transmitter/receiver unit 204B. The management unit 202 may further include digital processor 240 for storage of analyte data and/or related information, carrying out calculations and processing of the analyte data and/or related information, and transmitting the analyte data and/or information for display on the visual display 214. The management unit may also include a memory 242. The memory 242 can include any of the types of memory mentioned above for the interchangeable transmitter/receiver unit 204B, but may also include a flash memory device, such as a universal serial bus (USB) flash drive, or a memory card. USB flash drives are also known as thumb drives, handy drives, flash sticks, or jump drives. Memory cards may have a variety of formats, including PC Card (PCMCIA), CompactFlash (CF), SmartMedia (SM/SMC), Memory Stick (MS), Multimedia Card (MMC), Secure Digital Card (SD), xD-Picture Card (xD), Intelligent Stick (iStick), ExpressCard, or variations thereof. In some embodiments, the memory 242 may include execute-in-place (XIP) memory, such as NOR (NOR digital logic gate) flash memory. It is also contemplated that the memory 242 may employ other storage media, such as a floppy disk or an optical disc (CD, DVD, Blu-ray disc).

The management unit 202 may also include a suitable battery/power source 246. For example, the management unit 202 may include a rechargeable battery or other power components. The battery/power source 246 may include power management, which may distribute power from the respective power source 246 to the processor 240 as well as to other system components. The power management, for example, can be configured to enter a standby mode to minimize power use when the management unit 202 is idle. If a rechargeable battery is employed, a charger 248 (e.g., a charging circuit) may be employed to accomplish recharging of the battery/power source 246 by interfacing with a conventional charger base unit 250.

The management unit 202 may include a visual display 214, which may include any suitable type of display technology. Examples of a suitable visual display 202 include a Liquid Crystal Display (LCD), a Light Emitting Diode (LED) display, Organic Light Emitting Diode (OLED) display, Chip On Glass (COG) display, or the like. Any suitable display capable of displaying the analyte data and/or related information may be used.

As illustrated, the management unit 202 may interface with and download information from an analyte meter (not shown) through auxiliary interface 252. The auxiliary interface 252 may be any suitable component or collection of components to connect with the BGM, such as a USB cable and receiving electronics enabling communication with the processor 240.

The management unit 202 is adapted to receive the data representative of a concentration of analyte present in the bodily fluid from the on-body sensor 206. The actual calculation of the concentration of analyte from the reaction measured by the on-body sensor 206 may be accomplished by the processor 232, which may execute programmed instructions according to a measurement algorithm or algorithms contained in software 236 of the interchangeable transmitter/receiver unit 204B. The methods and sensors for generating and calculating the analyte values are conventional and will not be further described herein. Analyte data and related information processed by the digital processor 232 may be stored locally in the memory 234.

As each reading is received in memory 234, the reconfigurable transceiver 230, in this case configured as a transmitter of the interchangeable transmitter/receiver unit 204B, may send a wireless signal via the antennas 231 to the interchangeable transmitter/receiver unit 204A, as indicated by wireless communication signal line 231A. The signal 231A is received by the interchangeable transmitter/receiver unit 204A and is stored in memory 242 and may be immediately displayed on the visual display 214, or later at the command of the user, for example.

In some embodiments, the memory 242 may store software 244. The software 244 may include software programs associated with a health data management application (hereinafter "health data management software"). The health data management software may be a program or collection of programs or computer codes that receives and processes the measured analyte data and/or other related data (e.g., dates, times) from the reconfigurable transceiver 230, and/or other user provided input (e.g., insulin or medication dosage, meal information, exercise information, etc.) and/or other user-defined input. The health data management software may process the input of analyte data, and/or related information in a manner that is desired by the user such that the data and/or its derivative(s) may be displayed on the visual display 214. This collective health information may be used by, for example, a user, home care provider (HCP), and/or a physician.

FIG. 7A illustrates a method aspect according to some embodiments of the present invention. Broadly, the method 700A is an analyte data communication method. The method 700A includes, in block 702, transmitting analyte data from a first interchangeable wireless transmitter/receiver unit which is coupled to an on-body sensor, and, in block 704, receiving the analyte data from a first interchangeable wireless transmitter/receiver unit at a second interchangeable transmitter/receiver unit that is coupled to a management unit. The interchangeable wireless transmitter/receiver units are preferably substantially identical to one another. The interchangeable wireless transmitter/receiver units may be interchanged with one another as needed, such as when the interchangeable transmitter/receiver unit attached to the on-body sensor is to undergo charging. The interchangeable wireless transmitter/receiver units 204A, 204B when switched with one another may be reconfigured as either a transmitter or a receiver. The reconfiguration may be performed mechanically (e.g., via flipping a switch), by communication between the processors (e.g., 232, and 240), or by software.

In some embodiments, software may include a program adapted to configure the interchangeable transmitter/receiver unit 204A and the interchangeable transmitter/receiver unit 204B appropriately as a transmitter or receiver depending upon whether the unit 204A, 204B is attached to the on-body sensor 206 or to the management unit 202. A connection of the unit 204A, 204B to a component (e.g., connection to the management unit or on-body sensor) may be determined and a configuration may be set based upon a sensed connection. For example, a load, voltage, or current level may be sensed or detected by the unit 204A, 204B. Based on the level of the sensed parameter, a configuration of the unit 204A, 204B as a transmitter or receiver may be set. Optionally, communication between the processors 232, 240 may be established upon attachment of the unit 204A onto the management unit 202, and once established, the reconfiguration as a receiver may take place.

Additionally, in some embodiments, the unit 504C may include strip reading capability and may be configured as a stand-alone BGM (see FIGS. 5E-5F) as will be described further herein below.

Figure 8:
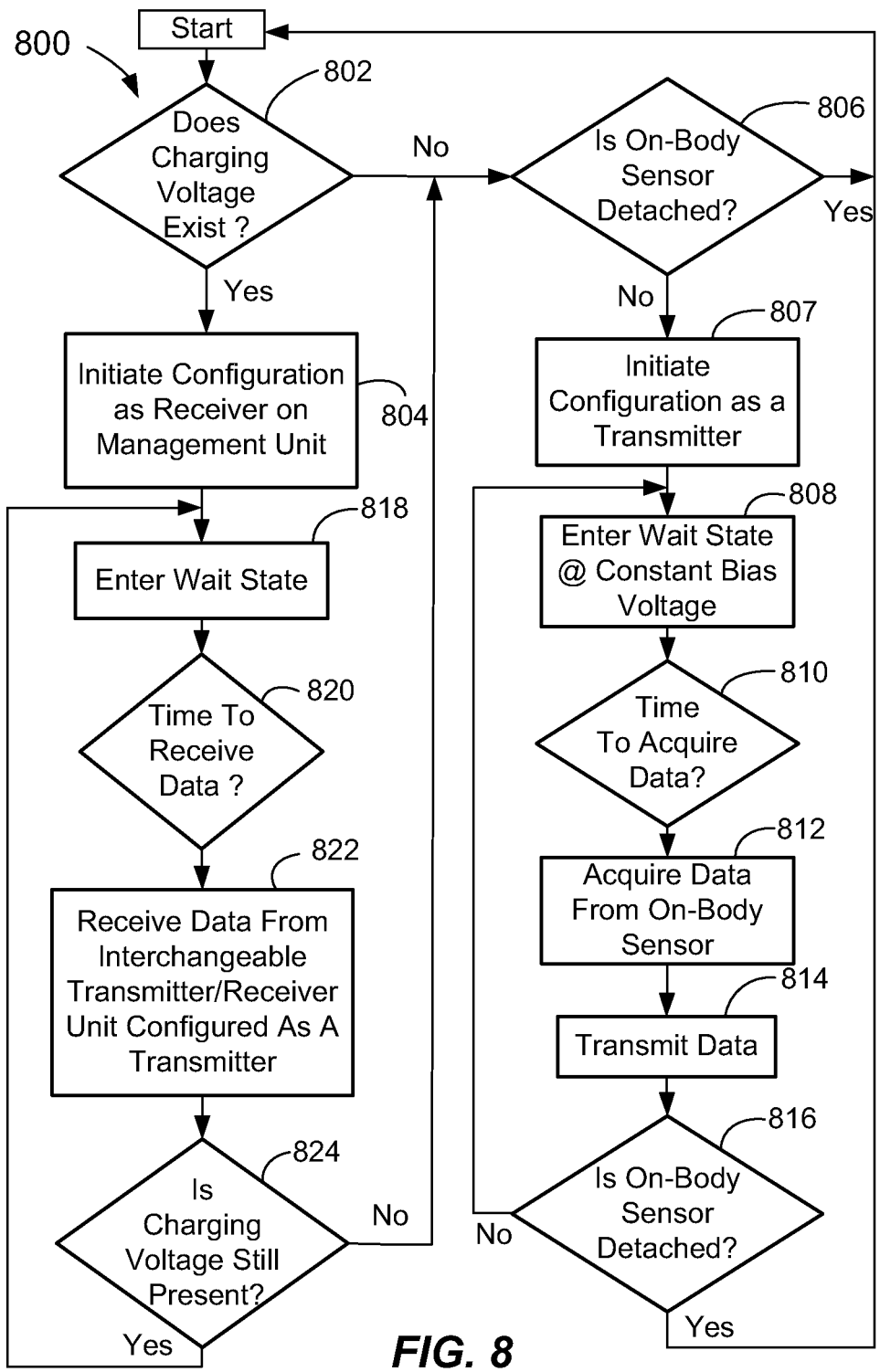
FIG. 8 is a flowchart illustrating programming steps used to configure an embodiment of a reconfigurable transceiver/receiver according to the present invention.

In FIG. 8, the configuration as a receiver when resident on the management unit 202, or as a transmitter when resident on the on-body sensor 206, may be determined by the method 800 outlined in the flowchart. For example, in some embodiments, the configuration may be set dependent upon whether a charging voltage exists. For example, in block 802, the program may first check to see if a charging voltage exists. This may be determined by a simple circuit provided in the charger 239. For example, if a charging voltage is detected that is above a threshold by power control and sensing electronics of the charger 239, then the reconfigurable transceiver 230 is initially configured as a receiver in block 804 because the unit 204A is mounted to the management unit 202. If a charging voltage above the threshold does not exist, then the unit may be configured as a transmitter, i.e., as interchangeable transmitter/receiver unit 204B if an on-body sensor 206 is detected in block 806. If the unit is still detached (perhaps in transit—not yet installed on the sensor pod 207) then the program continues again at start. If the on-body 206 is not detached, i.e., the unit is coupled to the on-body sensor 206, than the unit may be therefore configured as a transmitter in block 807. The determination of whether the on-body sensor 206 is detected in block 806 may be by any suitable means, such as by providing a short pulse of low voltage (e.g., 0.1 V) to the electrical connectors on the unit which are adapted to electrically couple to on-body sensor 206 and detecting a response therefrom in a suitable circuit (e.g., a bridge or other detection circuit). Once it is determined that the on-body sensor 206 is not detached, the configuration as a transmitter may be initiated in block 807.

The act of configuration as a transmitter in block 807 may involve setting a timing window for transmitting data. For example, the program may set the timing window such that data (e.g., a raw signal from the on-body sensor 206) or a data set is acquired from the on-body sensor 206 in block 812 at a desired time interval based upon an internal clock of the processor 232 determining it is time to acquire data in block 810 and then acquiring data in block 812 and transmitting the data in block 814 every few seconds, every minute, or every few minutes, for example. Preferably, the step of acquiring the data in 812 and transmitting the data in 814 are provided one after another and without appreciable delay. Other time periods may be used. The time period between the data being acquired in block 812 and transmitted in block 814 for a first acquired piece of data or data set until the next acquired piece of data or data set is referred to herein as "wait time." During the wait time, the unit 204B may be configured in a wait state as in block 808. During the wait state, a voltage bias may be provided to the on-body sensor 206 as described below. The configuration as a transmitter may also include a setting, selection, or establishment of a transfer function to be used in converting a raw signal from the on-body sensor 206 to an actual value, such as when some calculation is to be undertaken (e.g., a calculation of a interstitial fluid glucose value). As mentioned above, the configuration may also include setting an appropriate voltage bias for the sensor 206. Such bias may be a constant voltage (e.g., 0.3 volts) applied to the contacts of the on-body sensor 206 during the wait time, for example. Optionally, the bias voltage may be powered down during the wait state in some configurations to save power, wherein the bias may only be provided when an actual digitized raw signal reading is being taken. At the end of the program, another detection step (e.g., step 816) may be undertaken to determine if the on-body sensor 206 is detached from the unit 204B. If NO, then the unit 204B again enters the wait state, waiting for the next time window for which to acquire and transmit data as in blocks 812, 814. If the answer in block 816 is YES, then there may be a likelihood that the unit 204B is in transit to be charged (exchanged with unit 204A) or is being mounted to the management unit 202.

In the case where the interchangeable transmitter/receiver unit 204A is received on the management unit 202 and a charge voltage is detected in block 802 from the management unit power source 246, the interchangeable transmitter/receiver unit 204A is configured as a receiver in block 804. The act of configuration as a receiver in block 804 may involve setting the timing window for receiving data. For example, the program may set the timing window such that data (e.g., a raw signal from the on-body sensor 206) is acquired in a predetermined time window based upon an internal clock of the processor 232. The time period between the data being received in block 822 for a first acquired piece of data or data set until the next acquired piece of data or data set is received in 822 is also referred to herein as "wait time." The wait time may be set to any suitable period of time, such as several seconds, a minute, several minutes, etc. The wait time for the configuration as a receiver or as a transmitter is preferably the same, such that transmitting and receiving of data occurs within the window. The configuration step may also include the setting, or establishment of a transfer function to be used to convert a raw signal sent from the interchangeable transmitter/receiver unit 204B to an actual value. For example, the sent signal may be a raw digitized signal directly correlated to the current produced by on-body sensor 206. The transfer function may convert that signal to a measured interstitial fluid glucose value, for example. This interstitial fluid glucose value may be stored in memory 242 and/or displayed to the user on display 214. The configuration may also include setting a voltage bias to zero when configured as a receiver.

Once configured, the interchangeable transmitter/receiver unit 204A then may enter into a wait state in block 818. The period of wait may be set during the initial configuration of the unit as interchangeable transmitter/receiver unit 204A. At the configured time window, as indicated by block 820, data may be acquired (received) in block 822 from the interchangeable transmitter/receiver unit 204B as it is transmitted in block 814. After transmitting and receiving the data, a check may be undertaken to determine if a charging voltage is still present in block 824. If a charging voltage does exist, then the transmitter/receiver unit 204A may again enter the wait state in block 818 and may stay in that state until the next time for receiving data as indicated by block 820 as based on the configured wait time. This loop may continue as long as the transmitter/receiver unit 204A is mounted in the management unit 202 and a suitable charging voltage is detected.

In block 824, if no voltage is detected, then the software assumes that the transmitter/receiver unit 204A is being interchanged and moved to be coupled to the on-body sensor 206. Thus, the unit is then configured as a transmitter in block 807, i.e., configured as transmitter/receiver unit 204B. The software keeps cycling until either a charging voltage is detected in block 802 or an on-body sensor 206 is detected in block 806.

As the data is transmitted to the corresponding transmitter/receiver unit 204A configured as a receiver, the receiver unit may send, and the transmitter unit may receive, an acknowledgement signal thereby acknowledging the receipt of data. Additionally, synchronization may take place between the reconfigurable transceivers 230 of the units 204A, 204B such that the timing (e.g., clocks) of each remain synchronized. Synchronization may occur at each exchange, every few exchanges, or as needed, for example. The actual signal exchange may be by any known telemetric communication protocol or transfer standard such as described above.

As used herein, being configured as a receiver means that the reconfigurable transceiver 230 is configured in a manner where the transceiver 230 is adapted to receive analyte data (either raw or calculated) and/or related information (e.g., date and/or time stamps, etc.). As used herein, being configured as a transmitter means that the reconfigurable transceiver 230 is configured in a manner where the transceiver 230 is adapted to transmit analyte data and/or related information (e.g., date and/or time stamps, etc.). In other words, acknowledgements and or synchronization signals may be needed for the communication to take place, but they are not analyte data and/or related information that is being received or transmitted, but it is only received and transmitted as part of the communication protocol and to ensure that the paired RF transceivers 230 are properly communicating.

Figure 9:
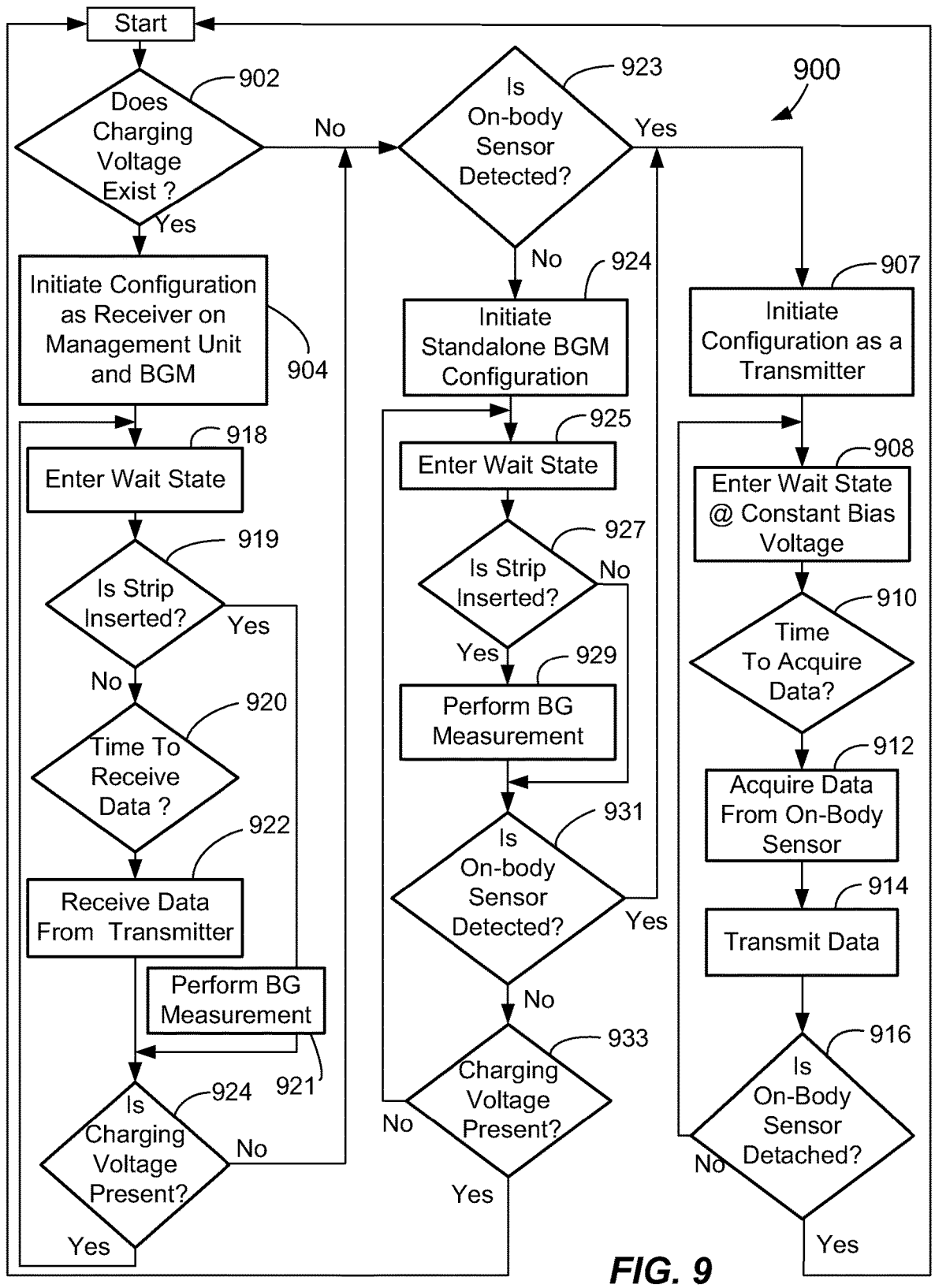
FIG. 9 is a flowchart illustrating programming steps used to configure another embodiment of a reconfigurable transceiver/receiver according to the present invention.

FIG. 9 is a flowchart which illustrates the configuration method 900 of the embodiments of FIGS. 5A-5F. Like the previously-described embodiment, the configuration program starts by trying to determine if a charging voltage exists in block 902. If charging voltage above a threshold exists, then the unit is configured as a receiver unit 204A and also as a blood glucose meter (BGM) 504A in block 904. After this, the receiver unit 504A enters into a wait state for the configured amount of time in 918. The wait state configuration in this embodiment is in a constant state of readiness to accept and test an analyte sensor (e.g., a test strip 125). Even though the unit 504A is in a wait state insofar as it is waiting to receive analyte date from the transmitter unit 204B, if it is determined that a strip 125 is inserted into the unit 504A in block 919, then the unit 404A undergoes a blood glucose (BG) measurement in block 921. In this manner, the unit 504A has the same capability as a reader unit of a conventional BGM. Of course, the invention is not restricted to only usage as a BGM, but may operate to monitor/test for any analyte of interest as mentioned above.

Figure 5D:
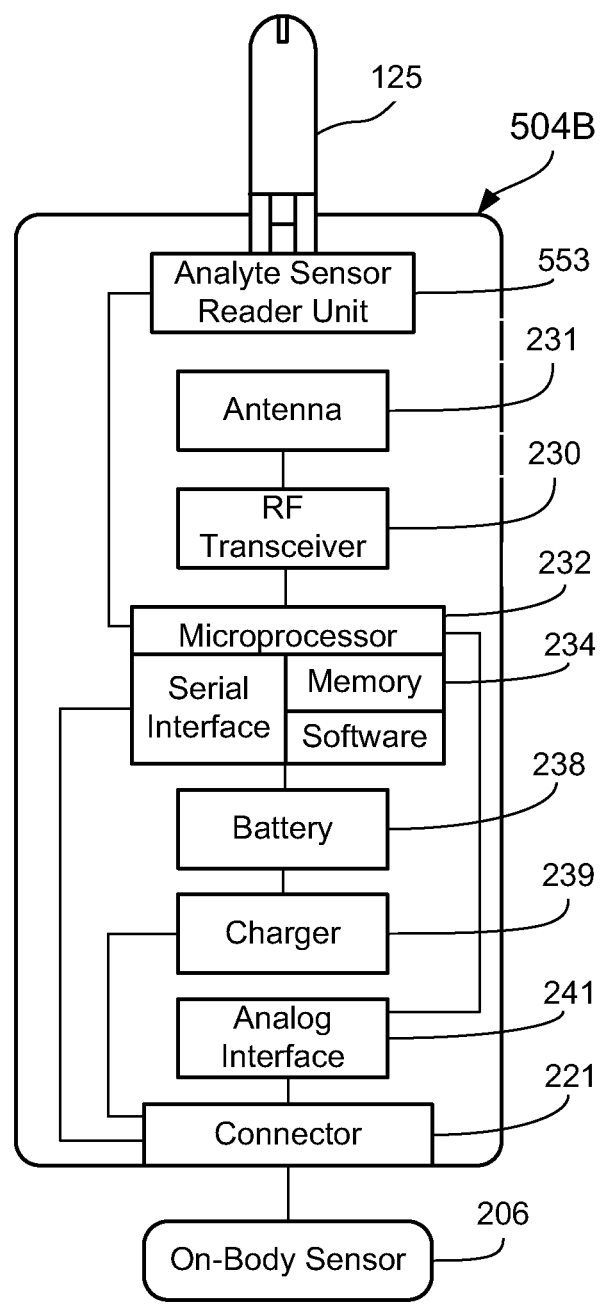
FIG. 5D is a block diagram illustrating another embodiment of an exemplary reconfigurable transceiver/receiver unit having test sensor capability according to the present invention.

In the unit 504C shown in FIGS. 5E and 5F, a display 554, such as a simple low power display, may display the analyte reading on the unit 504C itself. In this embodiment, the unit 504C may also be configured as a standalone BGM unit 504C. In this manner, the unit 504C may be used as a BGM (e.g., as a trusted BGM whose data may be used for calibration purposes). The remainder of the components of the unit 504C is the same as described with reference to FIGS. 5A-5D.

Again referring to FIG. 9, when it is determined in block 923 that no on-body sensor is detected after previously determining that no charging voltage exists in 902, then the unit is configured as a standalone BGM configuration in block 926. In one embodiment, the transmitter function may be turned off. Once being configured in the standalone configuration in 926, the unit 504C enters into a wait state in block 925. In this state, the unit 504C is readied, and when it is determined that a strip 125 is inserted in block 927, a BG measurement then takes place in block 929. Again, the routine may check the state to determine if an on-body sensor 206 is detected in 931. If it is, then the unit is attached to the on-body sensor 206 and may be configured as a transmitter in block 907. The unit then enters the wait state 908 as previously described with reference to FIG. 8. At the configured time as determined in block 910 the data is acquired from the on-body sensor 206 in block 912 and transmitted in block 914. In block 916, a check may take place to see if the on-body sensor 206 is detached. If the determination is NO, then the wait state is again entered until the time for transmitting the next reading. If it is determined that the on-body sensor 206 is detached from the unit, then the routine returns to start. In this manner, it should be apparent that the unit may be reconfigurable as a receiver, as a standalone BGM, or as a transmitter, depending upon whether the unit is coupled to the management unit 502, coupled to nothing (standing alone and detached), or coupled to the on-body sensor 206. If in block 931 the on-body sensor 206 is not detected, then in block 933 it is tested if there is any charging voltage present. If NO, then the unit remains configured as a standalone BGM 504C. If YES, then the routine goes back to start because the unit is either in transit or being coupled to the management unit 202. If a charging voltage is sensed in 902, then the unit is configured as a receiver in 904. As previously described with reference to FIG. 8, the unit 504A is in a wait state in regards to the receipt of data from the unit 504B in block 918. At the allotted time, it is determined that it is time to receive data in 920, and data is received in 922 shortly thereafter and within the receiving window. After this, a check for voltage is performed in block 924. If NO, then the routine proceeds to check for an on-body sensor connection at 923. If YES, then the unit remains configured as a receiver unit 504A.

As described above, the measured analyte data and/or related information from a determination of an analyte in a user's bodily fluid by the on-body sensor 206 may be generated by and transferred to the management unit 202. As one example, the analyte data only may be transmitted. The data (e.g., raw data, a calculated concentration of an interstitial fluid, or a glucose analyte concentration) may be transferred and then coupled and stored with related information, such as a date and time stamp generated by the management unit 202 and other information that may be input by a user via user interface 216, such as meal times, etc. Advantageously, the health data management software 244 resident in memory 242 may provide for, and allow, advanced displays and data processing that may be desired by a user.

In accordance with another embodiment, as best shown in FIGS. 3A-3D, the management unit 302 may be further adapted to receive and test an analyte level of a body fluid applied to an analyte test sensor 125. The analyte sensor 125 (sometimes referred to as a "test strip" or "test sensor") may be received in an analyte sensor reader unit 353 of the management unit 302. The analyte sensor reader unit 353 is of conventional construction and includes all components enabling communication between the sensor 125 and the processor 340.

The test sensor 125 may be an electrochemical test sensor or a photochromic test sensor, for example. An electrochemical test sensor typically includes a plurality of electrodes and a fluid-receiving area that contains a reagent. Upon contact with analyte of interest (e.g., glucose) in a fluid sample (e.g., blood) an electrical current may be produced, which may be proportional to an analyte concentration level in the fluid sample. The reagent may contain an enzyme such as, for example, glucose oxidase. However, it is contemplated that other reagents may be used to react with the analyte, depending on the analyte desired to be measured. In general, the reagent may be selected to react with the desired analyte or analytes to be tested to assist in determining an analyte concentration in a fluid sample. If the concentration of another analyte other than glucose is to be determined, an appropriate enzyme may be selected to react with the analyte.

Alternatively, the test sensor 125 may be a photochromic test sensor. Photochromic test sensors may use techniques such as, for example, transmission spectroscopy, diffuse reflectance, or fluorescence spectroscopy for measuring an analyte concentration. An indicator reagent and an analyte in a sample of body fluid may be reacted to produce a chromatic reaction, wherein the reaction between the reagent and analyte causes a color change. The degree of color change is indicative of the analyte concentration in the body fluid. The color change may be evaluated to measure the absorbance level of the transmitted light to determine a level of the analyte.

Some commercially available test sensors that may be used by the embodiments described herein include those that are available commercially from Bayer HealthCare LLC (Tarrytown, N.Y.). These test sensors include, but are not limited to, those used in the Bayer CONTOUR® blood glucose monitoring system, the Bayer BREEZE® and BREEZE®2 blood glucose monitoring system, and the Bayer Elite® and Elite® XL blood glucose monitoring system. It is contemplated that other test sensors, in addition to the ones listed above, may be incorporated into the methods and systems of the present invention. In some embodiments, the port 352 may be internal to the body 310 of the management unit 302 and the test sensor 125 may be dispensed from a cartridge housed within the management unit housing 310. Cartridge based systems are described in U.S. Pat. No. 5,575,403, for example.

In this embodiment, the management unit 302 includes the added functionality of an analyte meter. The management unit 302 in this embodiment is adapted to receive the test sensor 125 and generate (e.g., calculate), store in memory, and display (e.g., as a picture) on the visual display 314, the analyte data alone, analyte data and related information in various combinations, or the related information alone. The measured analyte data may include an analyte concentration value measured from a bodily fluid sample (e.g., blood, blood serum, blood plasma, urine, or interstitial fluid, etc.). For example, in some embodiments the analyte data can be a single interstitial fluid concentration value, or a single analyte concentration value (e.g., a single calculated glucose concentration value). Information related to the analyte value ("related information") may also be generated or provided, either alone or in combination with the analyte data.

Related information may consist of a measurement time (a time stamp) of the measurement of the analyte by the management unit 302, and/or a measurement date (date stamp) of the measurement of the analyte. Additional information may be provided such as a meal time associated with the measurement of the analyte, a meal marker associated with the measurement of the analyte (e.g., B-Breakfast, L-Lunch, D-Dinner, S-Snack), insulin or medication dosages associated with the analyte measurement, an average analyte concentration over a defined period of time, an indication of health status, e.g., feeling well, ill, stressed, fatigued, etc.

The analyte reading generated by measuring the analyte using the analyte sensor 125 may be used as a calibration reading, which may be used to normalize the repeated readings received by the interchangeable transmitter/receiver unit 204A from the interchangeable transmitter/receiver unit 204B. For example, a normalization factor may be generated and stored in memory 342, and used to adjust the analyte values received from the interchangeable transmitter/receiver unit 204B. This normalization factor may be used to adjust all the subsequent readings transmitted from the integrated transmitter/receiver unit 204B until the next calibration reading is taken by the user using the management unit 302 of the system 300. The additional components (the visual display 214, user interface 216, battery/power source 246, charger 248, connector 220, and charger base unit 350) are the same as described above for the FIG. 2F embodiment. The components of the units 204A, 204B in the FIG. 3D embodiment are the same as in the FIG. 2F embodiment.

FIGS. 4A-4D illustrate another embodiment of the system 400 including a management unit 402 with a detachable and interchangeable transmitter/receiver unit 404A and on-body sensor 206 with interchangeable transmitter/receiver unit 404B received in a sensor pod 207. In this embodiment, the interchangeable transmitter/receiver units 404A, 404B may each include a display 454. The display 454 may be a low cost, low power display such as a segmented LCD display. However, the display may also be a conventional Liquid Crystal Display (LCD), Light Emitting Diode (LED), Organic Light Emitting Diode (OLED), plasma, Chip On Glass (COG), Cathode Ray Tube (CRT), or the like. The display 454 may be provided in addition to the display 414 of the management unit 402 or as an alternative thereto (display 414 shown dotted to indicate it is optional). The other components (the reconfigurable transceiver 230, antenna 231, processor 232, memory 234, connector 221, battery 238, and charger 239) are the same as above described with reference to FIG. 2F. Additional software components to enable display of the obtained readings on the low power display 454 may be provided in software 436. Such software routines to display the interstitial fluid readings, being entirely conventional, will not be described further herein.

FIGS. 5A-5D illustrate another embodiment of the system 500 including a management unit 502 with a detachable and interchangeable transmitter/receiver unit 504A, and an on-body sensor 206 with interchangeable transmitter/receiver unit 504B received in a sensor pod 207. In this embodiment, the interchangeable transmitter/receiver units 504A, 504B may each receive, or be adapted to receive, an analyte sensor 125 in an analyte sensor reader unit 553 formed internally in the interchangeable transmitter/receiver units 504A, 504B. The management unit 502 may be provided with a suitable display 514. The other components (the connector 221, reconfigurable RF transceiver 230, antenna 231, processor 232, memory 234, battery 238, and charger 239) may be the same as described above.

Figure 6:
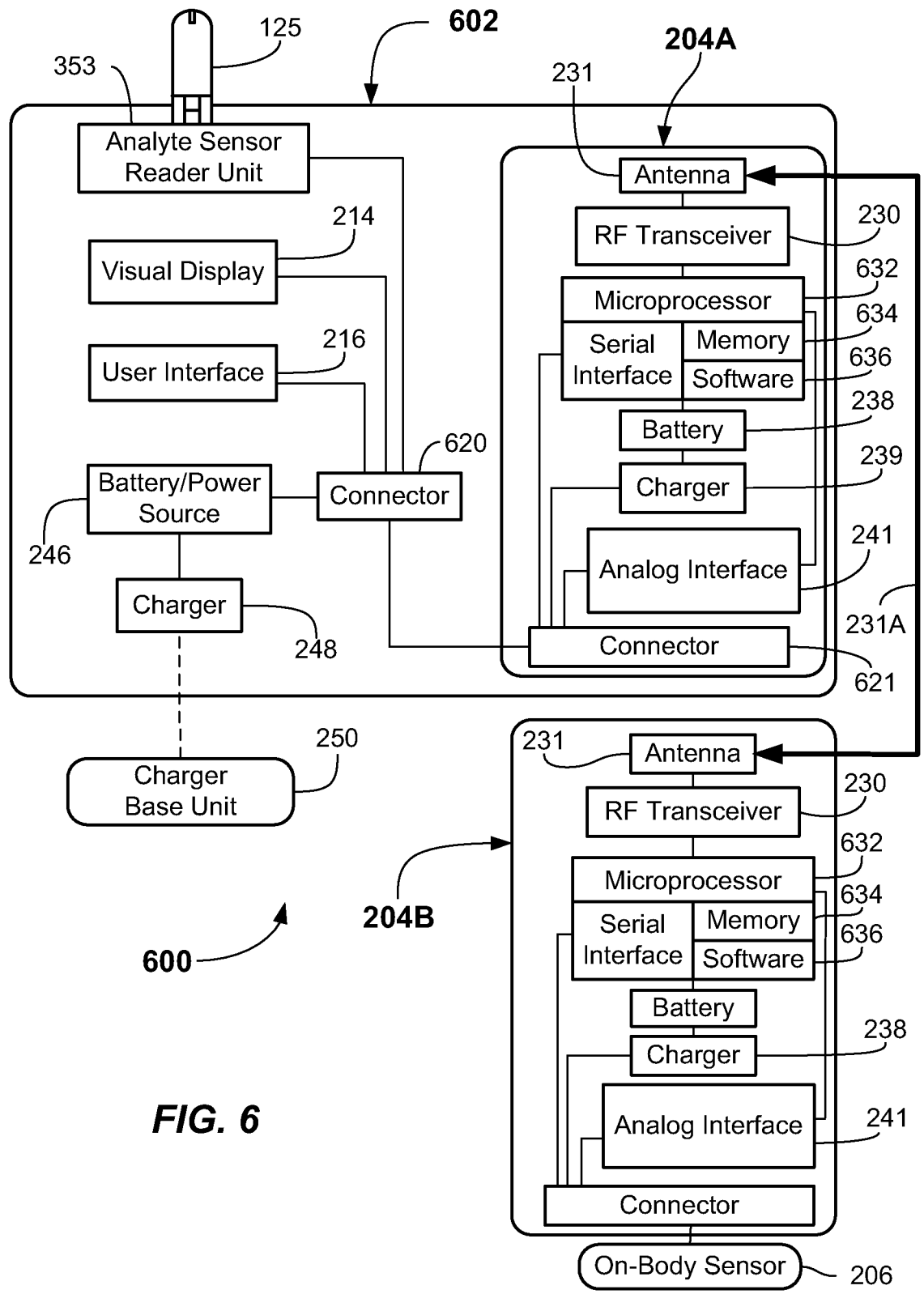
FIG. 6 is a block diagram illustrating another embodiment of system including a reconfigurable transceiver/receiver unit according to the present invention.
Figure 7:
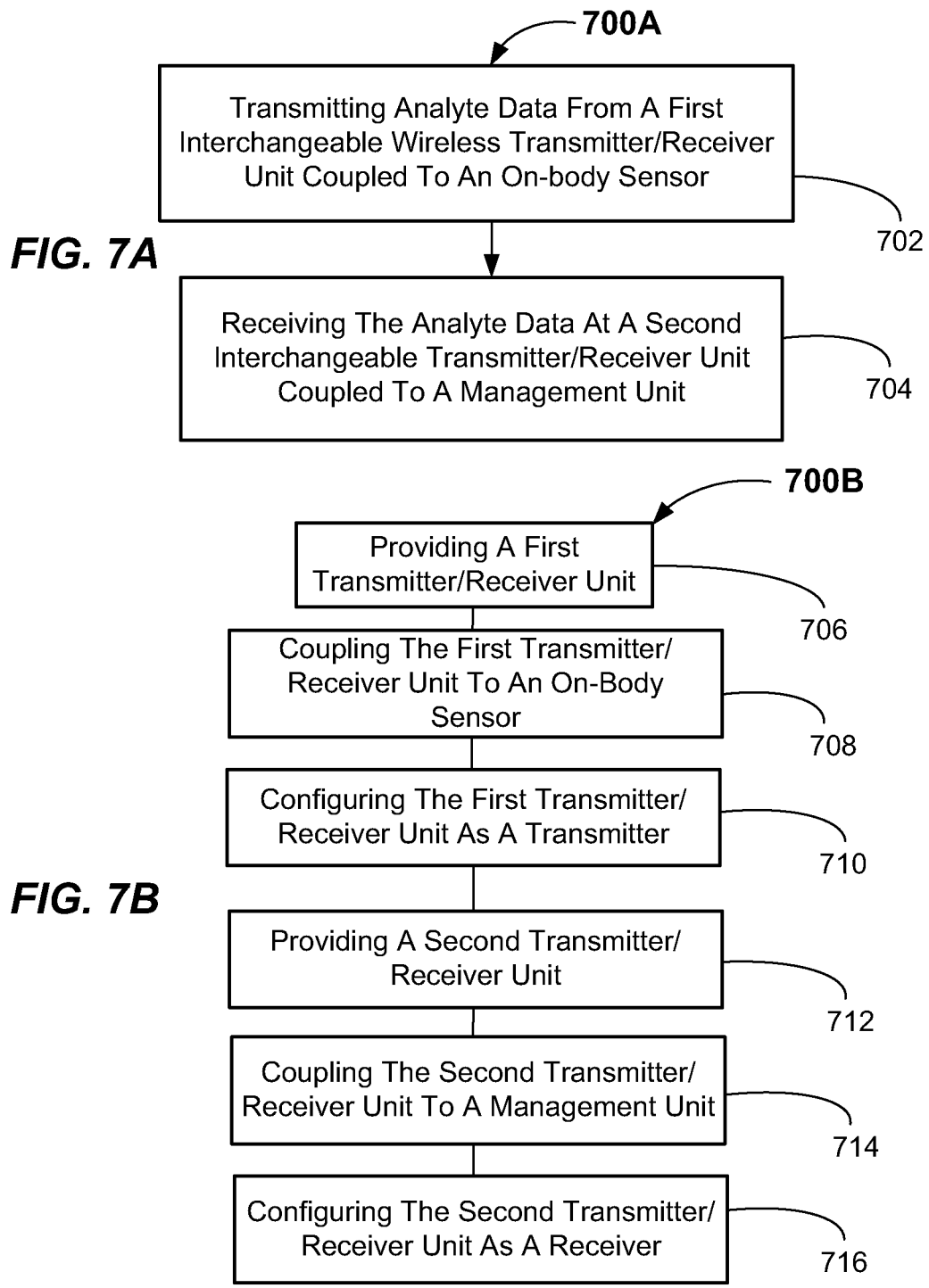
FIG. 7A is a flowchart illustrating a method according to embodiments of the present invention.
FIG. 7B is a flowchart illustrating another method according to embodiments of the present invention.

FIG. 6 illustrates another embodiment of the system 600 including a management unit 602 with a detachable and interchangeable transmitter/receiver unit 204A, and an on-body sensor 206 with interchangeable transmitter/receiver unit 204B received in a sensor pod 207 (see FIGS. 2A and 2B). In this embodiment, the interchangeable transmitter/receiver units 204A, 204B may each be identical, interchangeable, and reconfigurable as in the previous embodiments. The management unit 602 may be provided with a suitable visual display 214, a user interface 216, a battery/power source 246, and a charger 248. Additionally, analyte sensor reading capability may be included (such as described with reference to FIG. 3D) wherein an analyte sensor reader unit 353 is included that may couple to an analyte sensor 125. The other components of the interchangeable units 204A, 204B (the reconfigurable RF transceiver 230, antenna 231, processor 232, memory 234, battery 238, and charger 239) may be the same as described above. However, in the present invention, it should be apparent that the processor 632 that performs all the calculations and routines is resident on the interchangeable unit 204A, i.e., there is no processor dedicated only to the unit 602. In other words, the processer 632 of the unit 204A that is coupled to the management unit 602 comprises the only processor for the management unit 602. Accordingly, connectors 620, 621 allow communication between the various components (e.g., analyte sensor reader unit 353, visual display 214, user interface 216, etc.) and the processor 632, memory 634, and software 636. As in the previous embodiments, the analog interface 241 senses a condition of the component that it is connected to (the unit 602, or on-body sensor 206) and then software routines are selected in software 636 based upon the sensed condition.

For example, if an on-body sensor 206 is detected, then the unit 204B is configured as a transmitter and a transmitter routine sends data at the predetermined intervals. If the management unit 602 is detected, then the unit 204A is configured as a receiver, and a receiver routine may receive data at the predetermined intervals coinciding with the send intervals of the unit 204B. In embodiments where the analyte reader unit 353 is resident on the management unit 602, a software routine enabling the processor 632 to calculate analyte values may also be operative. In this way, the unit 204A may receive transmitted readings from the on-body sensor 206 and also calculate analyte values based upon a coupled analyte sensor 125. During the operation of the analyte sensor testing routine wherein a reading for an analyte sensor is determined, the receipt of the data from the on-body sensor 206 may be temporarily suspended.

Alternatively, the analyte sensor reader unit 353 and display 214, as shown in FIG. 6, may be included as part of the interchangeable units 204A, 204B, such as shown in the FIGS. 5E and 5F embodiment (see reader unit 553). In this embodiment, the management unit may only include a user interface 216, a charger 248, and a connector similar to connector 620 (but with the connection to an analyte sensor reader unit 353 and display 214 being removed). In this configuration, as in the FIGS. 5E and 5F embodiment, the unit may be configured as a stand-alone unit (e.g., 504C). In this configuration, no management unit or on-body sensor 206 is detected, so the routine for a stand-alone analyte meter may be accessed in software 236. In embodiments where a display 454 is provided on the interchangeable units 404A, 404B, 504C (FIGS. 4A-4D, and FIGS. 5E and 5F), when the unit is coupled to the on-body sensor 206, a software routine may be selected which both periodically or intermittently obtains and calculates an analyte reading. The reading may be displayed on the display of the unit 404B. This may be followed or preceded by operation as a transmitter where the data is sent from unit 404B to the unit 404A. The analyte reading may be displayed by the unit 404A in addition to being displayed on unit 404B, or in lieu of being displayed thereon.

The operation of the data communication method in accordance with an aspect of the invention will now be described in more detail with reference to FIGS. 7A and 7B. Referring to FIG. 7A, the analyte data communication method 700A operates between the interchangeable transmitter/receiver unit (e.g., 204A, 304A, 404A, 504A) coupled to the management unit (e.g., 202, 302, 402, and 502) and the transmitter/receiver unit (e.g., 204B, 304B, 404B, 504B) coupled to the on-body sensor 206. The method 700A includes in 702 transmitting analyte data from a first interchangeable wireless transmitter/receiver unit coupled to an on-body sensor, and, in 704, receiving the analyte data at a second interchangeable transmitter/receiver unit coupled to a management unit (e.g., 202, 302, 402, and 502).

In another method aspect, as described with reference to FIG. 7B, the method includes providing a first transmitter/receiver unit (e.g., 204B, 304B, 404B, 504B) in 706, coupling the transmitter/receiver unit to an on-body sensor (e.g., 206) in 708, configuring the first transmitter/receiver unit as a transmitter in 710, providing a second transmitter/receiver unit (e.g., 204A, 304A, 404A, 504A) in 712, coupling the transmitter/receiver unit to a management unit (e.g., 206) in 714, configuring the second transmitter/receiver unit in 716 as a receiver.

While the invention is susceptible to various modifications and alternative forms, specific systems, methods, and apparatus embodiments have been shown by way of example in the drawings and have been described in detail herein. It should be understood, however, that it is not intended to limit the invention to the particular systems, methods, and apparatus disclosed, but, to the contrary, to cover all modifications, equivalents and alternatives falling within the scope of the invention.

What is claimed is:

1. An analyte data communication apparatus, comprising:
a wireless transmitter/receiver unit configured to be removably docked to an on-body sensor in one configuration and to a management unit in another configuration, the on-body sensor configured to sense data representing a concentration of an analyte present in bodily fluid and having no wireless transmitter/receiver capability, the management unit having no wireless transmitter/receiver capability, wherein the wireless transmitter/receiver unit:
provides the only wireless transmitter/receiver capability in the on-body sensor when docked thereto;
provides the only wireless transmitter/receiver capability in the management unit when docked thereto; and
operates as a transmitter, a receiver, or a stand-alone analyte meter based on a sensed dock connection by the wireless transmitter/receiver unit.

2. The apparatus of claim 1, wherein the wireless transmitter/receiver unit operates as:
a transmitter based on a sensed connection to the on-body sensor;
a receiver based on a sensed connection to the management unit; and
a stand-alone analyte meter based on a sensed connection to a test sensor.

3. The apparatus of claim 1, wherein the wireless transmitter/receiver unit comprises a rechargeable battery and receives an electrical charge from the management unit when docked thereto.

4. The apparatus of claim 1, wherein the wireless transmitter/receiver unit comprises an analyte sensor reader unit configured to receive a test sensor.

5. The apparatus of claim 1, wherein the wireless transmitter/receiver unit comprises a visual display and is operative to display a measured analyte value.

6. The apparatus of claim 1, wherein the wireless transmitter/receiver unit comprises a processor, a memory, a transceiver, an antenna, and a rechargeable battery.

7. The apparatus of claim 1, wherein the wireless transmitter/receiver unit comprises a processor and provides via the processor the only processing capability in the management unit when docked thereto.

8. The apparatus of claim 1, further comprising the on-body sensor having the wireless transmitter/receiver unit docked thereto, the on-body sensor configured to be connected to a person's body and to be in communication with body fluid of the person, the on-body sensor further configured to transmit analyte data via the wireless transmitter/receiver unit.

9. The apparatus of claim 1, wherein the wireless transmitter/receiver unit is configured to be received in a sensor pod connected to the on-body sensor.

10. The apparatus of claim 1, further comprising the management unit having the wireless transmitter/receiver unit docked thereto, the management unit configured to function as a continuous glucose monitor (CGM) receiving a continuous or semi-continuous flow of analyte data via the wireless transmitter/receiver unit.

11. The apparatus of claim 10, wherein the management unit comprises an analyte sensor reader unit configured to receive a test sensor.

12. An analyte data communication apparatus, comprising:
a wireless transmitter/receiver unit configured to be interchangeably and removably docked to an on-body sensor in a first configuration to transmit a wireless signal, and configured to be interchangeably and removably docked to a management unit in a second configuration to receive a wireless signal, wherein the on-body sensor is configured to sense data representing a concentration of an analyte present in bodily fluid, the management unit has no wireless transmitter/receiver capability, the first and second configurations are based upon a sensed dock connection by the wireless transmitter/receiver unit, and the wireless transmitter/receiver unit provides the only wireless transmitter/receiver capability in the management unit when docked thereto.

13. The apparatus of claim 12, wherein the wireless transmitter/receiver unit comprises a processor and provides via the processor the only processing capability in the management unit when docked thereto.

14. The apparatus of claim 12, wherein the wireless transmitter/receiver unit comprises a rechargeable battery and receives an electrical charge from the management unit when docked thereto.

15. The apparatus of claim 12, wherein the wireless transmitter/receiver unit is configured to operate as a stand-alone analyte meter.

16. The apparatus of claim 12, wherein the sensed connection is determined via detection of a charge voltage.

17. A communication method for communicating analyte data, comprising:
    providing an interchangeable wireless transmitter/receiver unit configurable as either a transmitter or a receiver based on a sensed connection;
    configuring the interchangeable wireless transmitter/receiver unit as a transmitter in response to the interchangeable wireless transmitter/receiver unit sensing a connection to an on-body sensor;
    transmitting analyte data detected by the on-body sensor from the interchangeable wireless transmitter/receiver unit in response to configuring the interchangeable wireless transmitter/receiver unit as a transmitter;
    configuring the interchangeable wireless transmitter/receiver unit as a receiver in response to the interchangeable wireless transmitter/receiver unit sensing a connection to a management unit; and
    receiving analyte data at the interchangeable wireless transmitter/receiver unit in response to configuring the interchangeable wireless transmitter/receiver unit as a receiver, the management unit having no wireless transmitter/receiver capability until the interchangeable wireless transmitter/receiver unit is removably docked to the management unit.

18. The method of claim 17, further comprising reconfiguring the interchangeable wireless transmitter/receiver unit from a transmitter to a receiver in response to sensing a subsequent connection from the on-body sensor to the management unit.

19. The method of claim 17, further comprising reconfiguring the interchangeable wireless transmitter/receiver unit from a receiver to a transmitter in response to sensing a subsequent connection from the management unit to the on-body sensor.

20. The method of claim 17, further comprising charging a rechargeable battery of the interchangeable wireless transmitter/receiver unit via an electrical charge received from the management unit in response to sensing the connection to the management unit.

* * * * *